US006864240B1

(12) United States Patent
John et al.

(10) Patent No.: US 6,864,240 B1
(45) Date of Patent: Mar. 8, 2005

(54) DIPEPTIDE INHIBITORS OF β-SECRETASE

(75) Inventors: Varghese John, San Francisco, CA (US); Jay Tung, Belmont, CA (US); Roy Hom, San Francisco, CA (US); Ashley Guinn, Pacifica, CA (US); Lawrence Fang, Foster City, CA (US); Andrea Gailunas, San Francisco, CA (US); Shumeye S. Mamo, Oakland, CA (US)

(73) Assignee: Elan Pharmaceuticals, Inc., So. San Francisco, CA (US)

( * ) Notice: Subject to any disclaimer, the term of this patent is extended or adjusted under 35 U.S.C. 154(b) by 201 days.

(21) Appl. No.: 09/594,978

(22) Filed: Jun. 15, 2000

Related U.S. Application Data
(60) Provisional application No. 60/173,354, filed on Dec. 26, 1999, and provisional application No. 60/139,190, filed on Jun. 15, 1999.

(51) Int. Cl.$^7$ ................................................. C07K 5/06
(52) U.S. Cl. ........................ 514/19; 562/553; 530/331; 530/332
(58) Field of Search ........................... 514/19; 562/553; 530/331, 332

(56) References Cited

U.S. PATENT DOCUMENTS 4,709,010 A    11/1987 Holzemann et al. ........ 530/323

FOREIGN PATENT DOCUMENTS

WO    WO 97/30072    8/1997

OTHER PUBLICATIONS

Dominguez D. I., Amyloid 8 (2) 124_42, 2001.*
Wolfe, J. Med. Chem. 44, 2039, 2001.*
Wilkinson, Chem. Eng. News 45–57, 2002.*
Tung Jay S, J. Med. Chem. 45 (2) 259–62, 2002.*
Ghosh A K, J. Med. Chem. 44(18) 2865–8, 2001.*
Turner R. T., Biochemistry 40 (34) 10001–6, 2001.*
Majer, Pavel, et al., "Structure–based subsite specificity mapping of human cathepsin D using statine–based inhibitors" *Protein Science*, 6:1458–1466 (1977).

* cited by examiner

*Primary Examiner*—Jon P. Weber
*Assistant Examiner*—David Lukton
(74) *Attorney, Agent, or Firm*—McDonnell Boehnen Hulbert & Berghoff LLP

(57) ABSTRACT

Dipeptide derived inhibitors of the β-secretase enzyme are provided which are useful in the treatment of Alzheimer's disease and other diseases characterized by deposition of Aβ peptide in a mammal. The compounds of the invention provide useful methods of treatment by administration of these inhibitors to reduce Aβ peptide formation and in pharmaceutical compositions.

37 Claims, No Drawings

DIPEPTIDE INHIBITORS OF β-SECRETASE

This application claims the benefit of U.S. Provisional Application No. 60/139,190, filed Jun. 15, 1999 and No. 60/173,354, filed Dec. 26, 1999.

FIELD OF THE INVENTION

This invention is directed to compounds useful in treatment of Alzheimer's disease and more specifically to compounds which are capable of inhibiting β-secretase, an enzyme that cleaves amyloid precursor protein to produce Aβ peptide, a major component of the amyloid plaques found in the brains of Alzheimer's sufferers.

BACKGROUND OF THE INVENTION

Alzheimer's disease (AD) is a progressive degenerative disease of the brain primarily associated with aging which results in loss of memory and orientation. As the disease progresses motor, sensory and linguistic abilities are also affected until there is global impairment of multiple cognitive functions of the brain. These cognitive losses occur gradually, but typically lead to severe impairment and eventual death in the range of four to twelve years.

Alzheimer's disease is characterized by two major pathologic observations in the brain: neurofibrillary tangles and amyloid (or neuritic) plaques. Neurofibrillary tangles occur not only in Alzheimer's disease but also in other dementia-inducing disorders, while amyloid plaques are peculiar to AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Neurofibrillary tangles are characterized as networks of microtubules and microfilaments which were once structural supports running symmetrically through the nerve cells transporting nutrients, but have degenerated into dysfunctional tangled masses. They can be described histologically as non-membrane bound bundles containing paired, helically wound filaments (PHF) that are approximately 10 nm in length and located in the perinuclear cytoplasm of certain neurons. Major components of paired helical filaments are highly phosphorylated tau proteins (PHF-tau) of 60 kDa, 64 kDa and 68 kDa. Tau belongs to the family of microtubule-associated proteins and plays a role in the microtubule assembly and stabilization. In certain other neurodegenerative disorders, including corticobasal degeneration (CBD), progressive supranuclear palsy (PSP) and Pick's disease, hyperphosphorylated tau proteins also accumulate in brain tissue in association with abnormal filaments. Recent research indicates that the pattern of hyperphosphorylation and the resulting ultrastructure of the helical filaments are somewhat different in each type of disease.

Amyloid plaques, on the other hand, are peculiar to and a defining feature of AD. Amyloid plaques are predominantly composed of amyloid beta peptide (Aβ, also sometimes designated as βA4). Aβ peptide is derived by proteolysis of the amyloid precursor protein (APP) and is comprised of 39–42 amino acids. Several proteases called secretases are involved in the processing of APP. It appears that the abnormal processing and deposition of Aβ in areas of the brain responsible for cognitive activities is a major factor in the development of AD. Cleavage of APP at the N-terminus of the βA4 peptide by β-secretase and the C-terminus by one or more γ-secretases constitutes the amyloidogenic pathway, i.e. the pathway by which Aβ is formed. Cleavage of APP by α-secretase and the same or a different gamma secretase produces α-sAPP, a secreted form of APP that does not result in amyloid plaque formation. This alternate pathway precludes the formation of Aβ peptide. It has been proposed that Aβ peptide accumulates as a result of the abnormal processing of APP by B-secreatase and that therefore inhibition of the activity of this enzyme involved in Aβ peptide production is desireable for treatement of AD. See for example, β-*Amyloid and Treatment Opportunities for Alzheimer's Disease*, Sabbagh, M., et al., Alz. Dis. Rev. 3, 1–19, (1997). Several lines of evidence indicate that progressive cerebral deposition of particular amyloidogenic peptides, β-amyloid peptides, (Aβ), play a seminal role in the pathogenesis of AD and can precede cognitive symptoms by years or decades. See, Selkoe, Neuron 6:487 (1991). Recently, it has been shown that .Aβ is released from neuronal cells grown in culture and is present in cerebrospinal fluid (CSF) of both normal individuals and AD patients. See, Seubert et al., Nature 359:325–327 (1992).

Although Aβ peptide is also produced in normal individuals, it is produced in greater quantities and often in a slightly different form in those people who will develop or who already have AD. Although diffuse deposition of Aβ peptide occurs in most all humans with aging, the formation of amyloid or neuritic plaques occur only in AD patients. Formation of these plaques is believed to occur over a period of years or even decades. The Aβ peptide in amyloid plaques is always folded in a particular three-dimensional pattern called a beta-pleated sheet and appears to be chemically modified as well, which could explain the association of the Aβ peptides into the larger, denser plaques, rather than the diffuse deposits normally seen. Associated with this central core of Aβ peptide in the amyloid plaque are surrounding abnormal neurites and several types of altered glial cells. Glial cells normally associate with neurons and perform support and protective functions. On the outside of the plaque are reactive astrocytes, which are a type of glial cell typically found in injured brain areas. Additionally many other biochemical components, including enzymes, proteoglycans and apolipoproteins are present in the plaques. For a discussion of the formation of these plaques see for example: Sabbagh, M., et al., cited supra.

The neurons touching the amyloid plaques are progressively debilitated and ultimately die. At present it is not known whether the Aβ peptide is neurotoxic in itself or if the secondary features of the amyloid plaques, e.g. the abnormal glial cells, cause the nerve cells to die. Researchers have demonstrated that the Aβ peptide has neurotoxic effects in vitro. Still other researchers have demonstrated that the 25–35 amino acid sequence of Aβ is similar to that of substance P, an endogenous neuropeptide compound present in certain brain tissues and having neuroexcitatory effects. Co-administration of substance P in the study blocked the neurotoxic effect of Aβ in rats. See: *An in vivo model for the neurodegenerative effects of beta amyloid and protection by substance P*. Kowall N W, et al., Proc Natl Acad Sci USA 88 (16) p7247–51 (1991). Another study reports that Aβ peptide is neurotoxic through its interference with $Ca^{++}$ homeostasis. Korotzer A. R., et al., *Differential regulation by beta-amyloid peptides of intracellular free Ca2+ concentration in* cultured rat microglia. Eur. J. Pharmacol., 288 (2):125–30 1995. Further, some studies have proposed that Aβ is responsible for the hyperphosphorylation of tau, a microtubule associated protein, which results in formation of PHFs and neurofibrillary tangles as described above. Thus, with Aβ peptide clearly linked to the formation of amyloid plaques and implicated in the formation of neurofibrillary tangles in AD, there is a need for agents and methods for reduction of Aβ in vivo.

At present there are no published means for specifically inhibiting the β-secretase enzyme, or even structural identification of the β-secretase enzyme is or a peptide sequence of its active site. However, a commonly assigned application naming John Anderson, Guriqbal Basi, et al. as inventors and entitled: β-Secretase Enzyme Compositions and Methods, identifies the enzyme and methods of use thereof and has received a utility filing number of Ser. No. 09/501,708. Additionally, a commonly assigned application naming Varghese John, Jay Tung, Shumeye Mamo and Larry Fang as inventors and entitled: Tetrapeptide Inhibitors of β-Secretase, describes and claims tetrapeptide inhibitors of the β-secretase enzyme and has provisional filing No. 60/139,173. The two above-identified applications are being filed on the same day as the present application. The contents of these co-pending applications are hereby incorporated by reference in their entirety for all purposes.

SUMMARY OF THE INVENTION

This invention is directed to the novel compounds that inhibit β-amyloid peptide production by preferentially binding to and inhibiting the proteolytic function of the β-secretase enzyme. Compounds of formula 1 possess β-secretase inhibitory activity:

Formula 1

A—N(R2)—CH(OH)—CH2—C(O)—NH—CH(R1)—B wherein:
A is i)

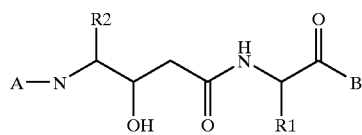

wherein Aryl is mono or bicyclic and has from 5 to 10 ring atoms and may optionally include up to 3 heteroatoms chosen from N, O and S;

each x is independently 0, 1 or 2;

R is H, $C_1$–$C_6$ alkyl, phenyl or benzyl wherein each phenyl ring is optionally substituted with up to two groups independently selected from —OH; —$CH_2OH$, —$CO_2H$, —$CF_3$, Cl, Br, F; and $C_1$–$C_2$ alkyl;

each $R_a$ is independently selected from the group consisting of H, OH, $C_1$–$C_3$ alkyl; $C_1$–$C_6$ alkylacylamino, $C_1$–$C_6$ alkylacyloxy, $C_1$–$C_6$ alkyloxy, $C_1$–$C_6$ alkylthioxy, amido (including primary, $C_1$–$C_6$ alkyl and phenyl secondary and tertiary), $NH_2$, mono and di($C_1$–$C_6$ alkyl and phenyl) amino, carbamyl (including $C_1$–$C_6$ alkyl and phenyl amides and esters), carboxyl (including $C_1$–$C_6$ alkyl and phenyl esters), carboxy ($C_2$–$C_5$)alkyloxy and N-heterocyclylacyl;

and n is 1 or 2;

ii)

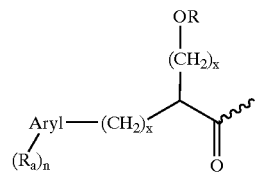

wherein D is chosen from aryl having 5 to 6 atoms, optionally including up to 2 heteroatoms selected from the N, O, and S; fused aryl of 8 to 14 atoms optionally including up to 3 heteroatoms selected from the N, O, and S; mono or fused cycloalkyl having 5 to 12 carbon atoms; and mono or fused heterocycloalkyl having 5 to 12 carbon atoms including up to 3 heteroatoms selected from N, O, and S; biaryl, diaryl ether; diarylketone, and phenyl($C_1$–$C_8$) alkyloxyaryl;

and wherein E is a divalent group chosen from carbonyl, sulfonyl, $C_1$–$C_3$ alkylene, —X—($C_1$–$C_3$) alkylcarbonyl wherein X is chosen from N, O and S, or E is merely a bond;

and D may optionally be substituted with up to two groups chosen from OH, $C_1$–$C_3$ alkyl; $C_1$–$C_6$ alkylacylamino, $C_1$–$C_6$ alkylacyloxy, $C_1$–$C_6$ alkyloxy, $C_1$–$C_6$ alkylthioxy, amido (including primary, $C_1$–$C_6$ alkyl and phenyl secondary and tertiary), $NH_2$, mono and di($C_1$–$C_6$ alkyl and phenyl) amino, carbamyl (including $C_1$–$C_6$ alkyl and phenyl amides and esters), carboxyl (including $C_1$–$C_6$ alkyl and phenyl esters), carboxy($C_2$–$C_5$)alkyloxy, N-heterocyclylacyl, $C_1$–$C_3$ alkylsulfonyl, sulfonamide and $C_1$–$C_3$ alkylsulfonamide;

iii) $C_1$–$C_6$ alkanoyl; $C_2$–$C_{-6}$ alkenoyl; and methylthio$C_1$–$C_5$ alkanoyl, any of which may be substituted with up to two groups chosen from OH, $C_1$–$C_6$ alkylacylamino, $C_1$–$C_6$ alkylacyloxy; $C_1$–$C_6$ alkyloxy; $C_1$–$C_6$ alkylthioxy, amido (including primary, $C_1$–$C_6$ alkyl secondary; $C_1$–$C_6$ alkyl and phenyl tertiary, amino, $C_1$–$C_6$ alkyl and phenyl amino, carbamyl (including $C_1$–$C_6$ alkyl and phenyl amides and esters), carboxyl (including $C_1$–$C_6$ alkyl and phenyl esters), carboxy($C_2$–$C_5$)alkyloxy and N-heterocyclylacyl, $C_1$–$C_3$ alkylsulfonyl, sulfonamide and $C_1$–$C_3$ alkylsulfonamide; and iv) a divalent group of the formula:

wherein each carbonyl of the divalent group bonds to the nitrogen to form a five membered ring and Ra is as defined above;

B is selected from —OH; $C_1$–$C_6$ alkyl or $C_1$–$C_6$ alkyl amino, di($C_1$–$C_6$ alkyl)amino, $C_1$–$C_6$ alkyloxy, N-heterocyclylic and

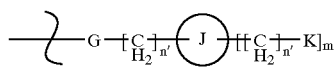

each n' is independently 0, 1 or 2;
m is 0, 1, 2 or 3;
and G is N or O;
J is selected from the group consisting of aryl having a 5 to 6 membered ring optionally including up to 2 heteroatoms selected from the N, O, and S; fused aryl rings of 8 to 14 atoms optionally including up to 3 heteroatoms selected from N, O, and S, mono or fused ring cycloalkyl having 5 to 12 carbon atoms; and mono or fused ring heterocyclic having 5 to 12 carbon atoms including up to 3 heteroatoms chosen from the group consisting of N, O, and S;
each K is chosen from OH, $C_1$–$C_3$ alkyl; $C_1$–$C_6$ alkylacylamino, $C_1$–$C_6$alkylacyloxy, $C_1$–$C_6$ alkyloxy, $C_1$–$C_6$ alkylthioxy, amido (including primary, $C_1$–$C_6$ alkyl and phenyl secondary and tertiary), $NH_2$, mono and di($C_1$–$C_6$ alkyl and phenyl) amino, carbamyl (including $C_1$–$C_6$ alkyl and phenyl amides and esters), carboxyl (including $C_1$–$C_6$ alkyl and phenyl esters) and carboxy($C_2$–$C_5$)alkyloxy;
R1 is straight or branched chain $C_1$–$C_5$ alkanyl or $C_2$–$C_5$ alkenyl;
R2 is $C_{1-5}$ straight or branched chain alkanyl or alkenyl; methylthiomethyl; aryl or arylalkyl or heteroaryl or heteroarylalkyl wherein any of the above are optionally substituted with up to 2 of $C_{1-3}$ alkyl, trifluoromethyl or halogen, and stereoisomers, hydrates or pharmaceutically acceptable salts thereof.

Preferred groups for R1 are ethyl and 2-propyl with 2-propyl being most preferred. Preferred groups for R2: 4-thiazolylmethyl, 4-methylphenylmethyl, and 2-methylprop-1-yl; more preferred are 2-thienylmethyl, 3-trifluoromethylphenylmethyl, and 3-chlorophenylmethyl and most preferred is 3,5-difluorophenylmethyl.

Preferred groups for A are substituted or unsubstituted 2-hydroxy-2-aryl-ethanoyls, carboxamidoarylcarbonyls, carboxamidopropionyls, sulfonamidopropionyls and carboxylarylcarbonyls. Most preferred are the 2-hydroxy-2-aryl-ethanoyls and substituted or unsubstituted 3-carboxamidoarylcarbonyls.

Preferred groups for B are substituted or unsubstituted aminomethyl-p-benzoic acids and esters, alkylamines, dicarboxycyclohexylamines, di- and trimethoxycyclohexylamines, di- and trihydroxymethylcyclohexyamines. More preferred are dicarboxycyclohexylamine, dimethoxycyclohexylamine and trimethoxycyclohexylamine. Most preferred are the 3,5-di- or 3,4,5-tri-substituted cyclohexylamines.

Inhibition of β-secretase enzyme halts or reduces the production of Aβ from APP and thus reduces or eliminates the formation of amyloid plaques and other types of Aβ deposition in the brain. Therefore, the compounds are useful in the prevention of Alzheimer's Disease in patients susceptible to AD and or in the treatment of patients already experiencing the effects of AD in order to inhibit ether deterioration in their condition. Now it has been discovered that the compounds of the present invention provide inhibitors of the β-secretase enzyme. Accordingly, in another aspect of this invention there are provided methods of treating a mammal having symptoms or at risk of developing the symptoms of Alzheimer's disease.

The method of treating Alzheimer's disease or Down's syndrome comprises administering to a mammal in need thereof a therapeutically effective amount of a β-secretase inhibitor of formula 1 above or pharmaceutically acceptable salts thereof to reduce the formation of Aβ peptide.

Still further, it is an object of the present invention to provide pharmaceutical compositions containing such β-secretase inhibitors of formula 1 above in a pharmaceutically acceptable carrier for use in the methods disclosed herein. Other objects of the invention will become apparent from reading the specification and the appended claims.

DETAILED DESCRIPTION OF THE INVENTION

Natural amino acids are available in abundance, and a great array of non-naturally occuring amino acids have been prepared by techniques well known to those skilled in the art of organic synthesis. Roberts and Vellaccio provide a comprehensive listing of non-natural amino acids, and techniques for the synthesis of many variations thereof in *The Peptides*, Vol. 5: Analysis, Synthesis, Biology; Academic Press, NY 1983. A more recent description of additional routes to chirally pure non-natural amino acids is in: *Asymmetric synthesis of α-amino acids from carbohydrates as chiral templates*; Cintas, P. Tetrahedron, 47 (32), 6079–111 (1991). Thus one skilled in the art can synthesize the amino acid precursors used in the preparation of the compounds of the invention by a judicious selection of one or more of the methods outlined above, which articles are hereby incorporated by reference.

Statine is a non-standard amino acid residue present in pepstatin that provides this peptide its inhibitory activity (Rich, D. H., *J. Med. Chem.* 28, p. 262 (1985). Interestingly, pepstatin has no inhibitory activity in assays with β-secretase. Statine has the chemical name (3S,4S)-4-amino-3-hydroxy-6-methylheptanoic acid, and is further identified in the Merck Index (11th ed.) at monograph no. 8759, and is available commercially, such as through the Sigma-Aldrich catalog. The three letter abbreviation given to statine in the peptide art is Sta. The (3S,4S) stereoisomer is designated Sta(s) or statine(s). Statine derivatives are also well known in the literature and can be prepared by methods disclosed in U.S. Pat. No. 4,397,786. Other methods are described in the series cited above (The Peptides, Vol. 5: Analysis, Synthesis, Biology; Academic Press, NY 1983] and by Bringmann et al. in Synlett (5), pp. 253–255 (1990); by Kessler and Schudok in Synthesis (6) pp. 457–8 (1990); and by Nishi and Morisawa in Heterocycles 29(9), 1835–42 (1989).

Optical Isomers-Diastereomers-Geometric Isomers

Some of the compounds described herein contain one of more asymmetric centers and may thus give rise to enantiomers, diastereomers, and other stereoisometric forms which may be defined in terms of absolute stereochemistry as (R)- or (S)-, or as (D)- or (L)- for amino acids. The present invention is meant to include all such possible diastereomers and enantiomers as well as their racemic and optically pure forms. Optically active (R)- and (S), or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are intended to be included.

Stereoisomers refer to molecules wherein the same atoms attach to one other in the same order, but the positioning of the attachment varies so that two molecules may not be spatially identical; they are classified according to the number and symmetry of the chiral centers in each molecule. Chiral centers are atoms to which the same kinds of atoms are attached but have more than one possibility for arrangement around the chiral center atom. There are two types of stereoisomers: diastereomers and enantiomers.

Diastereomers are stereoisomeric two molecules having the same connectivity, but which are not mirror images of each other. Chiral centers in diastereomers are arranged so that an internal plane of symmetry exists in the molecule. The chemical and physical properties of diastereomers tend to differ because different spatial shape changes the ways in which the molecules interact.

Enantiomers are two molecules which are exact mirror images of one other, because each chiral center is a reflection of the chiral center of the other enantiomer. Enantiomers have very similar chemical and physical properties, which make separations based on their physical properties extremely difficult. Enantiomers are usually labeled R and S (for right-handed and left-handed) to distinguish them.

Racemic mixtures are defined as mixtures of two mirror image forms of the same molecule (enantiomers) in equal amounts.

Although stereoisomers may not vary greatly on a chemical level, on the biological level, different stereoisomers isomers "fit" differently into the various protein receptors that drive biochemical processes and thus stereoisomers, and frequently even enantiomers, do not bind equally. Therefore, enantiomers of the same compound can have different effects within the human body.

Unless defined otherwise, all scientific and technical terms used herein have the same meaning as commonly understood by one of skill in the art to which this invention belongs. All patents and publications referred to herein are hereby incorporated by reference for all purposes.

Many of the embodiments of the present invention embrace the residue—or side chain—of a naturally occurring α-amino acid, it is to be noted that each α-amino acid has a characteristic "R-group", the R-group being the residue—or side chain—attached to the α-carbon atom of the amino acid. For example, the residue of glycine is H, for alanine it is methyl, for valine it is 2-propyl, for methionine it is methylthioethyl. The specific residues of the naturally occurring α-amino acids are well known to those of skill in the art. See, e.g, A. L. Lehninger, Biochemistry: The Molecular Basis of Cell Structure and Function, 1975 (or any edition thereafter), Worth Publishers, NY, see, particularly Chapter 4). As used herein, the residues of naturally occurring α-amino acids are the residues of those about twenty α-amino acids found in nature which are incorporated into a protein by the specific recognition of the tRNA molecule with its cognate mRNA codon in humans.

Those non-naturally occurring α-amino acid residues embraced by the present invention are known to those of skill in the art. Statine, as discussed above in the background of the art is a commercially available γ-amino acid. In the compounds the preferred stereoisomer is the S configuration and the absolute stereochemistry is (3S,4S).

Other modified or non-usual amino acids are 2-aminobutyric acid (Abu) and phenylglycine (Phg), In amino acids of this type a change is made in the side chain of the amino acid, usually by varying the length or substitution thereon. For instance, 2-aminobutyric acid is an α-amino acid that varies from valine by the removal of one of the methyl groups from the side chain. Phenylglycine is a homolog of the naturally-occurring amino acid phenylalanine, which lacks the methylene linkage between the peptide backbone and the phenyl group found in phenylalanine. Norleucine (Nle) is a slightly different example where the branching methyl group of leucine is shifted rather than deleted to make a non-branching (normal) chain having the same number of carbon atoms as leucine. These unusual amino acids can be incorporated into peptide chains using the standard peptide linkage synthetic procedures described below for the naturally-occurring amino acids.

As used herein, the term "alkyl" includes the straight and branched-chain hydrocarbons having single bonds and double bonds, the number of carbons atoms being generally specified. Where not specified the alkyl groups preferably contain from about 1 up to about 12, more preferably 1 to 6. Exemplary of such moieties are methyl, ethyl, n-propyl, isopropenyl, n-butyl, t-butyl, sec-butyl, pentyl, n-hexyl, n-nonyl, n-decenyl, and the like. The term "lower alkyl" includes $C_1$–$C_5$ (i.e. 1 to 5 carbon atom) alkyl groups such as methyl, ethyl, n-propyl, isopropyl, n-butyl, s-butyl, t-butyl, n-pentyl, and the like.

As used herein, "heteroatom(s)" is/are selected from O, N or S, unless otherwise specified.

"Alkane "or" alkanyl" includes the straight and branched-chain hydrocarbons having all carbon-carbon single bonds, the number of carbons atoms being generally specified. Where not specified the alkane groups preferably contain from about 1 up to about 12, more preferably 1 to 6. Exemplary of alkanyl moieties are 2-methyl-propyl, 2-methylpentyl, n-butyl, 2,2-dimethylethyl (t-butyl), octyl, 4-ethyloctyl, and the like. "Alkylene" refers to a divalent alkyl chain, e.g. —$CH_2$—$CH_2$— or —$CH_2$—$CH(CH_3)$—$CH_2$—.

"Alkene "or" alkenyl" includes the straight and branched-chain hydrocarbons having at least one C—C double bond (>C=C<), number of carbons atoms being generally specified. Where not specified the alkene groups preferably contain from about 1 up to about 12, more preferably 1 to 6, and most preferably 1 to 5 carbons containing. Exemplary of alkenyl moieties are 2-methyl-2-propenyl, 2-methyl-1-propenyl, propenyl, 1-butenyl, 2-butenyl, 3-butenyl, 2,2-difluoroethenyl, 2,4-octadiene, as well as those straight and branched chained moieties having up to four double bonds.

The term "lower alkyl" includes $C_1$–$C_6$ alkyl groups such as methyl, ethyl, n-propyl, isopropyl, n-butyl, s-butyl, t-butyl, n-hexyl, and the like The term "halo" and "halogen" refer to chloro, bromo, fluoro, and iodo. Preferred among the halogens are fluoro, chloro and bromo.

"Lower alkenyl" refers to those $C_2$–$C_6$ unsaturated groups such as vinyl, 1-propene-2-yl, 1-butene-4-yl, 1-pentene-5-yl, 2-methyl-2-butene-4-yl and the like.

The term "alkyloxy" refers to those groups having an alkyl moiety from 1 to 6 carbon atoms linked to an oxygen atom. This oxygen is linked to the carbon atom of another group. Examples of alkyloxy groups are: methoxy, ethoxy, propoxy, butoxy, iso-butoxy, and the like. The term "alkenoxy" includes $C_2$–$C_6$ groups having a C—C double bond and an oxygen atom, such as ethenyloxy, propenyloxy, iso-butoxyethenyl and the like.

"Alkylthio" or refers to those groups having an alkyl moiety from 1 to 6 carbon atoms linked to a sulfur atom. This sulfur is linked to the carbon atom of another group. Methylthioalkyloxy" refers to the group "—O-alkylene-S-methyl" which includes by way of example, methylthioethoxy (—$OCH_2CH_2SCH_3$), and the like. Optionally, thioxy may also designate the same and is the sulfur equivalent of the "oxy" (alkenoxy, alkyoxy) groups defined above.

The term "amine" includes primary, secondary and tertiary amine which may be in straight or branched chains or, in the case of secondary and tertiary amines within rings, and are optionally substituted with $C_1$–$C_6$ acyloxy, $C_1$–$C_6$ alkyl and the like.

All the terms "carboxyl", "carboxylic acid", "carboxylate" and "carbamoyl" are terms referring to functional groups containing a carbon atom double-bonded to an oxygen atom [C=O, also called an acyl or a carbonyl group, represented in linear notation as —C(O)—] and additionally single-bonded to another oxygen atom [—C(O)—O—], and in the case of carbamoyl, additionally a nitrogen atom is also bonded to the carbonyl carbon to give —N—C(O)—O—. Carboxyl, carboxylate and carbamate include the corresponding pharmaceutically acceptable $C_1$–$C_6$ alkyl and $C_6$–$C_{10}$ aryl esters and secondary and tertiary amides.

Alkyl terms including the suffix "oyl" indicate the presence of a carbonyl group which bonds to another moiety. For example, alkanoyl indicates R—C(O)— where R is alkyl; ethanoyl indicates $CH_3$—C(O)—, and the like:

"Acyloxy" refers to the groups R—C(O)O—, substituted R—C(O)O—, cycloalkyl-C(O)O—, aryl-C(O)O—, and heterocyclic-C(O)O where R=alkyl, and alkyl, cycloalkyl, aryl, and heterocyclic are as defined herein.

"Acylamino" refers to the groups R—C(O)N—, substituted R—C(O)N—, cycloalkyl-C(O)N—, aryl-C(O)N—, and heterocyclic-C(O)N— where R=alkyl, and alkyl, cycloalkyl, aryl, and heterocyclic are as defined herein.

The terms "amide" and "amido" refer to a functional group containing a carbon atom double-bonded to an oxygen atom and additionally singly bonded to a nitrogen atom [—C(O)—N]. "Primary" amide describes an unsubstituted amide group [—C(O)—$NH_2$]. "Secondary" and "tertiary" amides are amides in which nitrogen is substituted with one and two non-hydrogen groups respectively. A tertiary amide may also be cyclic in the case where the amide nitrogen is in a ring and is referred to as "N-heterocyclylacyl". The term "lactam" refers to a cyclized amide, i.e. a secondary or tertiary amide wherein the carbonyl carbon and the nitrogen atom are adjacent members of a ring.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3enyl, cyclooct-3-enyl and the like.

The term "aryl" includes 3 to 8 membered stable saturated or unsaturated organic monocyclic rings having 0 to 4 hetero atoms selected from S, O, and N; and 7 to 10 membered organic stable, saturated or unsaturated, bicyclic rings having 0 to 5 hetero atoms selected from S, O, N; both of which may be substituted by halo, $C_1$–$C_6$ alkyl, $C_1$–$C_6$ alkoxy, $C_2$–$C_6$ alkenyl, $C_2$–$C_6$ alkynyl, substituted $C_1$–$C_6$ alkyl, $C_1$–$C_6$ substituted alkoxy, substituted $C_2$–$C_6$ alkenyl, or substituted $C_2$–$C_6$ alkynyl, hydroxy, amino, nitro, cyano, carboxy, hydroxymethyl, aminomethyl, carboxymethyl, $C_1$–$C_4$ alkylthio, $C_1$–$C_4$ alkanoyloxy, carbamoyl, or halo-substituted $C_1$–$C_6$ alkyl. The term "aryl" also includes fused ring carbocyclic and heterocyclic moieties having at least one aromatic nucleus.

The terms "arylalkyl" and "aralkyl" refer to any of the above aryl groups also having an alkyl radical that connects the aryl group to the larger structure.

Preferred aryl and aralkyl moieties are phenyl, benzyl, phenethyl, 1- and 2-naphthyl, naphthylmethyl, acenaphthyl, 5-, 6-, 7-, and 8-quinolinyl, benzofuryl, indenyl, or indanyl, benzimidazolyl, indolyl, benzothiophenyl, indole-3-ethyl and 5-, 6-, 7-, and 8-tetrahydroisoquinoline. Other examples of such ring systems may be found in J. Fletcher, O. Dermer, R. Fox, Nomenclature of Organic Compounds, pp. 20–63 (1974), and in the Examples herein.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring.

The terms substituted alkyl, substituted alkenyl, substituted alkynyl and substituted alkoxy are these radicals substituted with halogen, hydroxy, amino, $C_1$–$C_7$ acyloxy, nitro, carboxy, carbamoyl, carbamoyloxy, cyano, or $C_1$–$C_6$ alkoxy, and may be substituted one or more times with the same or a different group, preferably substituted 1 to 3 times.

"Sulfone" or "sulfonyl" refers to the divalent group $SO_2$, wherein each oxygen is bound to the central sulfur atom. Sulfonamide refers to the group —$SO_2$N—. A primary sulfonamide describes an unsubstituted amide group [—$SO_2$—$NH_2$]. "Secondary" and "tertiary" sulfonamides are amides in which nitrogen is substituted with one and two non-hydrogen groups respectively. A tertiary sulfonamide may also be cyclic.

A linking group is defined as a divalent linear chain facilitating the reach of a binding group, for example a carboxyl or an amide group to binding sites within the target protein. The facilitation occurs as a result of either or both the extension of the group at a particularly advantageous distance from another binding site on the molecule or in providing an advantageous flexibility to the group allowing adoption of a conformation that allows for optimal binding. Examples of the group Q which may be present in compounds of the invention include groups of formula: —$CH_2$—$(CH_2)_n$—; —O—$(CH_2)_n$—; NH—$(CH_2)_n$—; —O—$CH_2$—O—; —O—$CH_2$—NH—; NH—$CH_2$—NH— wherein n=0, 1 or 2.

It is also understood that there are known structures that are recognized in the art of medicinal chemistry as having similar properties and drug activities and are often substituted in the art for the more common moieties. These art recognized replacements are also within the scope of the invention. For example, there are a number of functional groups and rings that function as replacements for a carboxy group. Some of these moieties are, by way of example: tetrazole, hydroxamic acids, 5-hydroxyoxazoles, 3-sulfonyl-triazoles and beta-ketosulfonamides. Other equivalents are taught in *J. Med. Chem.* 1993, 31, 2485. Likewise, there are recognized equivalents in the art for the hydroxyl group of statine. These equivalents include an amino group, which was assayed and found to have inhibitory activity, (see for example: Jones, D. M., J. Peptide Res. 1997, 50, 109–121 and Arrowsmith, R. J., J. Chem. Soc., Chem. Commun., 1986, 755–757) as well as a geminal difluoro substitution on the hydroxyl bearing carbon. For example, Thaisrivongs, S., J. Med. Chem., 1987, 30, 1837–1842 teaches the use of difluorostatine in renin.

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc. A pharmaceutically acceptable excipient or diluent is any excipient which retains the activity of the therapeutic compound with which it is admixed and does not impart any deleterious or undesirable effect on the subject to whom it is administered and in the context in which it is administered.

Abbreviations used in this specification represent the following:

Ac=acetyl (methylcarbonyl)
aq.=aqueous
Boc=tert-butoxycarbonyl
BOP=benzotriazol-1-yloxy-tris(dimethylamino) phosphonium hexafluorophosphate
bd=broad doublet
bs=broad singlet
c=concentration (g/mL)
CBZ=benzyloxycarbonyl
cc=cubic centimeter
CDI=1,1'-carbonyldiimidazole
d=doublet
DMF=dimthylformaide
DMSO=dimethylsulfoxide
EDC=ethyl-1-(3-dimethylaminopropyl)carbodiimide or 1-(3-dimethylaminopropyl)-3-ethylcarbodiimide hydrochloride
EDTA=ethylene diamine tetraacetic acid
eq.=equivalents
EtOAc=ethyl acetate
EtOH=ethanol
g=grams
HOBT=1-hydroxybenzotriazole
h=hour
$IC_{50}$=inhibitory concentration of a compound where the enzyme activity is reduced by half.
L=liter
LDA=lithium diamine
m=multiplet
mass. spec. or MS=mass spectrum
max=maximum
mg=milligram
mL=milliliter
mm=millimeter
mM=millimolar
mmol=millimole
mp=melting point
MeOH=methanol
meq=milliequivalent
N=normal
ng=nanogram
nm=nanometers
nmr=nuclear magnetic resonance spectrum
OD=optical density
PEPC=1-(3-(1-pyrrolidinyl)propyl)-3-ethylcarbodiimide
pg=picoram
pM=picoMolar
psi=pounds per square inch
$R_f$=ratio of movement of a substance on a thin layer chromatogram in comparison to the movement of the solvent front.
δ=units of measurement for nuclear magnetic resonance spectroscopy which are relative to a standard, e.g. trimethyl silane.
q=quartet
quint.=quintet
rpm=rotations per minute
s=singlet
t=triplet
TEA=triethylacetate
TFA=trifluoroacetic acid
THF=tetrahydrofuran
TLC=thin layer chromatography
μL=microliter
μM=micromolar (an expression of concentration in micromoles/liter)
s=singlet
t=triplet
UV=ultraviolet A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc. A pharmaceutically acceptable excipient is any excipient which retains the activity of the therapeutic compound with which it is admixed and does not impart any deleterious or undesirable effect on the subject to whom it is administered and in the context in which it is administered.

The terms N-terminal or N-terminus refer to that terminal or end group of a peptide bearing the free or derivatized amino group of an amino acid residue. Likewise, C-terminal or C-terminus refers to that terminal or end group of a peptide bearing the free or derivatized carboxy group of an amino acid residue. The term "capping group" refers to a non-amino acid moiety bonded to the C- or N-terminal of the peptide chain. Examples of common N-terminal capping groups used in peptide synthesis are Boc (t-butoxycarbonyl,) and Cbz (benzyloxycarbonyl). Other capping groups useful in synthesis are acetyl and adamantyl. Non-limiting examples of capping groups useful in the present invention at both the C-terminal and N-terminal are shown in Table 1.

Methods of Synthesis

The following reaction scheme (1) illustrates the construction of the dipeptides derivatives herein and the variety of reactions that may be used to prepare intermediates from which compounds of Formula 1 may be prepared. Scheme 1 provides a generic method for the synthesis, but for convenience depicts statine and valine.

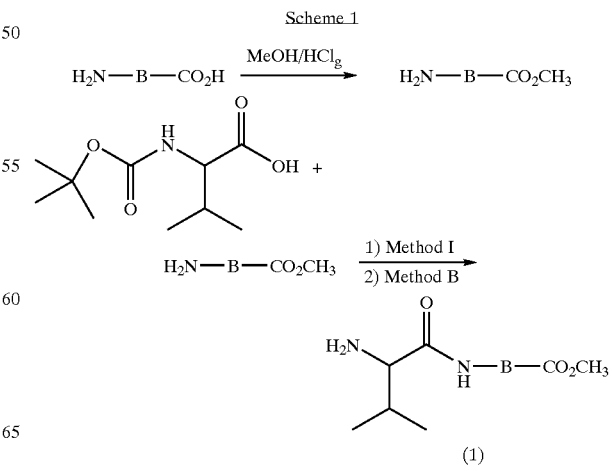

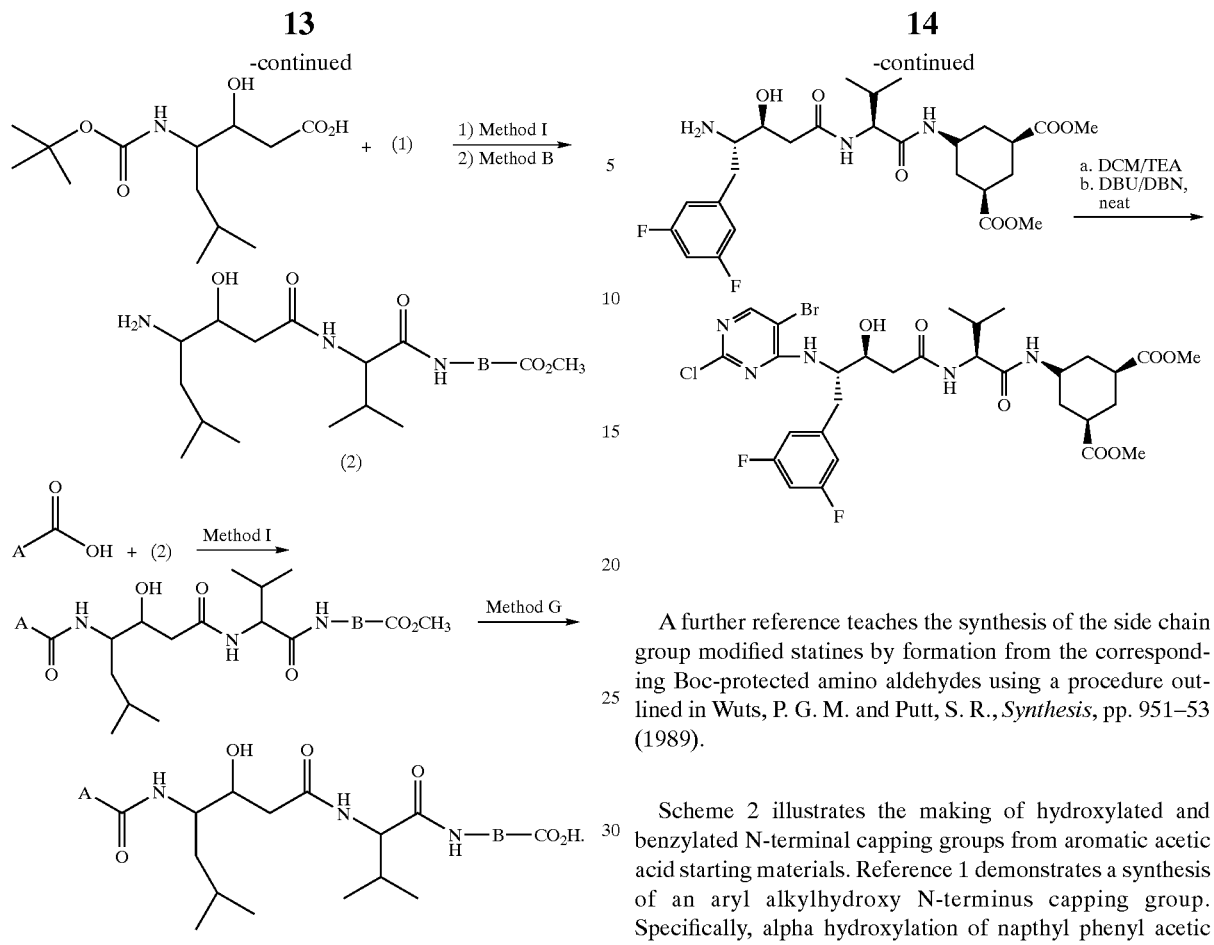

This scheme may be varied as desired by selecting a different carboxy protected amino acid residue, for example, α-amino-butyric acid (Abu) or phenylglycine (Phg) in Step A to couple with statine. Or alternatively, selecting a different statine derivative, such as Phe-Sta, wherein the 2-methyl-propyl group is replaced by benzyl, to be coupled with the starting amino acid in Step A. Derivatives of statine are known in the art and described in U.S. Pat. No. 4,397,786.

Derivatives of the N-terminal capping group may also be prepared by reducing or removing completely the amide bond. For example, reduction of the amido bond to a methylene amine or by bonding an aryl ring directly to the statine amino group (Scheme 1, compound (2)). Synthesis of the "deacylated" compounds may be effected by employing a directing group to increase the aryl halide reactivity, or reacting neat without solvents and using hindered bases such as DBU or DBN, as shown in Scheme 1B. Such reactions would yield the unsubstituted rings upon hydrogenation.

Scheme 1B

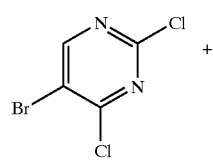

A further reference teaches the synthesis of the side chain group modified statines by formation from the corresponding Boc-protected amino aldehydes using a procedure outlined in Wuts, P. G. M. and Putt, S. R., *Synthesis*, pp. 951–53 (1989).

Scheme 2 illustrates the making of hydroxylated and benzylated N-terminal capping groups from aromatic acetic acid starting materials. Reference 1 demonstrates a synthesis of an aryl alkylhydroxy N-terminus capping group. Specifically, alpha hydroxylation of napthyl phenyl acetic acid, using lithium diethylamine and oxygen. Reference 2: demonstrates a synthesis of the corresponding benzyl ether from the α-hydroxyaromatic of Reference 1. [Reference 1. Moersch, G W, Zwiesler, M L. Synthesis, 1971, 647–648. Reference 2. Hon, Yung-Son, Chang, Rong-Chi, Chau, Tay-Yuan. Heterocycles, 1990, Vol. 31, No. 10, 1745–1750].

Scheme 2

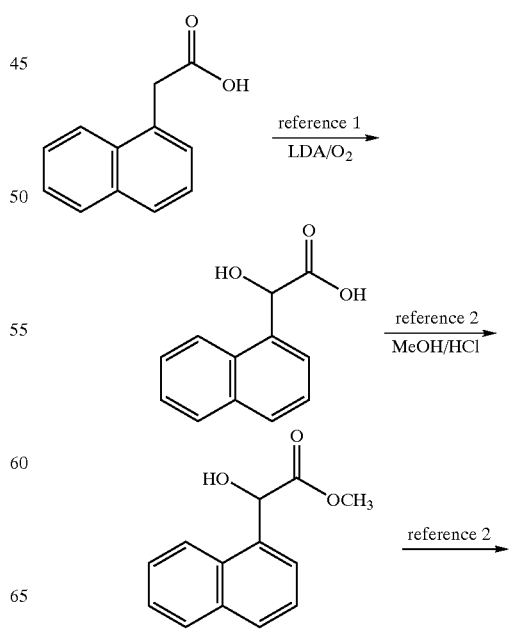

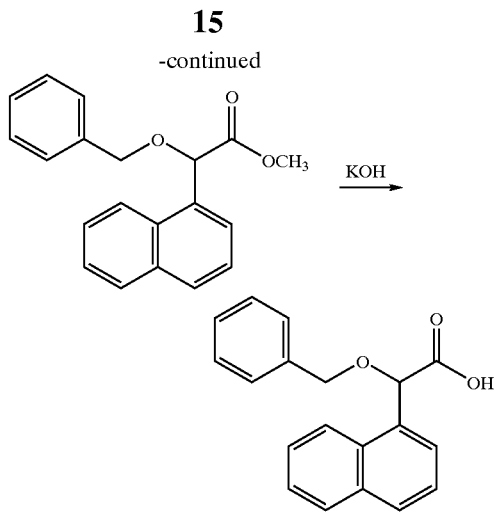

Experimental Methods

Step A

Coupling of the C-terminal amino acid with statine.

Boc-Sta(s) (1.0 equiv.) was dissolved in 30 mL of dry dichloromethane, then HOBT (2.0 equiv.), H$_2$N-Val-OBzl.HCl (1.0 equiv.) and TEA (5 equiv.) were added and the mixture was stirred for 20 minutes. EDC (1.2 equiv.) was then added and allowed to stir overnight under an atmosphere of nitrogen. The reaction was diluted with water and extracted with EtOAc (3×). The organic layers were washed with aqueous citric acid (2×), sat. NaHCO3 (2×), brine, then dried with MgSO$_4$.

Step B

Removal of the Boc-protecting group from the resulting dipeptide.

The Boc-protecting group of the dipeptide was dissolved in a trifluoroacetic acid/methylene chloride (1/1) solution. The reaction was monitored by TLC to confirm the consumption of starting material at which time the solvents were removed under reduced pressure to yield the free amine which was used without further purification.

Step C

Coupling deprotected amine with a selected N-terminal capping group.

For example, mandelic acid (1.0 equiv.) was dissolved in 30 mL of dry dichloromethane, then HOBT (2.0 equiv.), H$_2$N-Stat-Val-OBzl.HCl (1.0 equiv.) and TEA (5 equiv.) were added and all was stirred for 20 minutes. EDC (1.2 equiv.) was added and the mixture was stirred overnight under an atmosphere of nitrogen. The reaction was then diluted with water and extracted with EtOAc (3×). The organic layers were washed with aqueous citric acid (2×), sat. NaHCO3 (2×), brine, then dried over MgSO$_4$, and the solvent was removed under vacuum.

Step E

Removal of the Carboxybenzyl (Cbz) protecting group from the C-terminus

R-Stat-Val-OBz (1.2 g) was dissolved in 100 ml of MeOH and Pd/C (1 g, 10%) was added. The reaction was subjected to a hydrogen gas atmosphere of 50 psi for 2 hours. The resulting slurry was then filtered through a pad of celite, and rotary evaporated under reduced pressure to yield the desired carboxylic acid.

Step F

Coupling of the C-terminal end of the dipeptide with a functionalized amine

R-Stat-Val-OH (1.0 equiv.) was dissolved in 30 mL of dry dichloromethane, then HOBT (2.0 equiv.), H$_2$N—R (1.0 equiv.) and TEA (5 equiv.) were added and the reaction mixture was stirred for 20 minutes. EDC (1.2 equiv.) was added and allowed to stir overnight under an atmosphere of nitrogen. The reaction was diluted with water and extracted with EtOAc (3×). The organic layers were washed with aqueous citric acid (2×), sat. NaHCO3 (2×), brine, then dried over MgSO$_4$.

The amine groups (R—NH2) of the examples shown below are commercially available unless otherwise indicated by reference to a synthetic citation in a journal. Some of the compounds are supplied as the methyl ester of a carboxylic acid. If only the free carboxylic acid group is available commercially, the methyl ester can be prepared as indicated in step H below.

Step G

Cleavage of the C-terminal capping group methyl ester to provide free carboxylic acid or carboxylate salt The didpeptide methyl ester (1 equiv.) was dissolved in a suitable solvent (MeOH/water, dioxane/water, or THF/water). Hydroxide (2–20 equiv., KOH, NaOH, or LiOH) is added and the reaction mixture is allowed to stir until the all of the ester is converted to acid as evidenced by TLC. Volatile solvents were removed and the reaction was acidified with citric acid. The resulting precipitate was collected and characterized to insure the desired material is obtained.

Step H

Preparation of the methyl ester for the C-terminal capping reaction

For example, 4-aminomethylbenzoic acid was dissolved in dry methanol. HCL (gas) was bubbled through the mixture for 5 minutes. The reaction was then stirred overnight and rotoevaporated to yield the desired methyl 4-aminomethylbenzoate.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

Step J

Aminoaryl diesters to Aminocyclohexyl diesters

As an example of this ring hydrogenation, a preparation of dimethyl-aminophenyl-3,5-dicarboxylate is given. To the aromatic ester in acetic acid (12% v/v) was added 1.25 g of 5% rhodium on alumina (50% w/w), the mixed slurry was saturated with hydrogen at 55 psi and shaken for a total of 72 hrs. Upon completion of the hydrogenation the reaction was filtered through Celite and dried over anhydrous sodium sulfate. Filtration and subsequent rotoevaporation yielded crude product, which was then subjected to silica gel chromatographic purification to provide dimethyl aminocyclohexyl3,5-dicarboxylate as a pale white solid. See also: Fieser & Fieser, Reagents for Org. Syn. 4, 418 and Freifelder, M.; Ng, Y. H.; Helgren, P. F.; *J. Org. Chem.*, 30, 2485–6.

Step K

Formation of azide

As an example, the methyl ester of 4-bromomethylnaphthanlene-1-carboxylic acid (5.5 mmole) obtained in Step O (below) was dissolved in dry DMF and sodium azide (6.88 mmole) was added. The reaction was stirred overnight under nitrogen at 40° C. Workup: the reaction was concentrated under vacuum and partitioned between ethyl acetate and water. The organic layer was dried over MgSO$_4$ and the solvent removed under reduced pressure. The desired azide product was obtained in 89% yield.

Step L

Reduction of Azide

As an example, the methyl ester of 4-azidomethylnaphthanlene-1-carboxylic acid prepared in Step K (above) (2.44 mmole) was dissolved in THF, and $PtO_2$ (catalytic amount) was added. The reaction was shaken on a Parr apparatus in the presence of hydrogen (20–30 psi) for one hour. Workup: The solution was filtered through celite and was rinsed with methanol. The filtrate was concentrated down and the methyl ester of 4-aminomethylnaphthanlene-1-carboxylic acid was obtained in 92% yield. This amine was then utilized as a C-terminal capping group as described in Example 5.

Step M

Proctection of amine

As an example of amine protection by Boc derivitization, statine (9.9 mmole) and triethylamine (9.9 mole) were dissolved in dry dichloromethane and $(Boc)_2O$ was added. The reaction was stirred overnight under nitrogen. Workup: the reaction was concentrated on a rotary evaporator and the residue was taken up with ethyl acetate and then washed with water, citric acid, sodium bicarbonate, and brine. The organic solvent was dried over $MgSO_4$ to yield 86% of Boc-statine.

Step N

N-methylation

The dipeptide derivative (4.1 mmole) is dissolved in THF and methyl iodide is added, followed by sodium hydride. The reaction is stirred overnight under nitrogen. Workup: the reaction is concentrated on a rotary evaporator and the residue is taken up with ethyl acetate and then washed with water, citric acid, sodium bicarbonate, and brine. The organic solvent is dried over $MgSO_4$, solvent removed under reduced pressure to provide an N-methylated amide bond.

Step O

Bromination

For example, the methyl ester of 4-methylnaphthanlene-1-carboxylic acid (26.9 mmole), benzoyl peroxide (0.455 mmole), and NBS (26.9 mmole) were dissolved in benzene and kept at reflux overnight under $N_2$. After which the solution was concentrated down to dryness. The remaining solid was filtered and washed with hot water, then dried on high vacuum overnight (81%).

Steps K, L and O are employed in the order illustrated below in forming an aminomethyl substituent on aromatic rings.

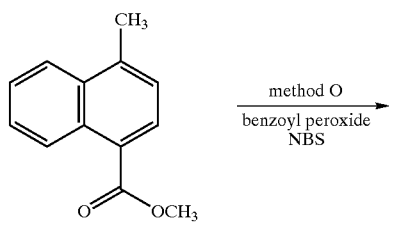

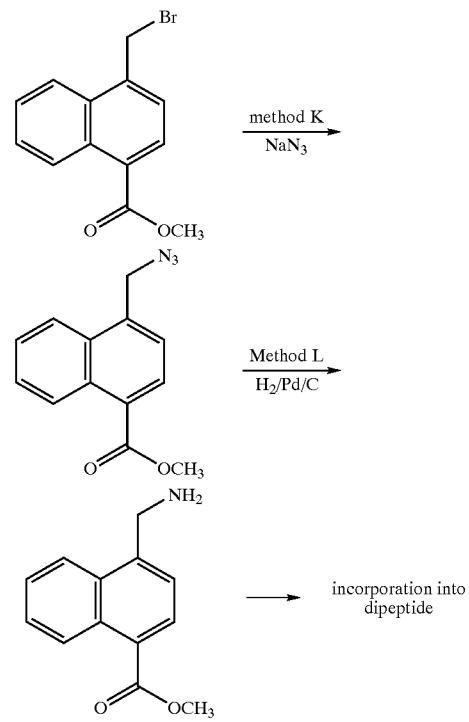

Step P

Statine derivatives

The synthesis of the side chain group modified statines by formation from the corresponding Boc-protected amino aldehydes according to a procedure of Wuts, P. G. M. and Putt, S. R., *Synthesis*, pp. 951–53 (1989) was utilized in making the 4-methylbenzyl, 2-thiophenylmethyl and 4-thiazolylmethyl and 3,5-difluoromethyl derivatives of statine. Scheme III demonstrates the sequence for construction of statine derivatives. Arylamino acids and functionalized arylamino acids are available from, for example, Synthetec, Albany, Oreg.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

For the purpose of classification of the inhibitor activities of the compounds of the present invention, the Examples given below have been grouped by their $IC_{50}$ concentrations. Those compounds of Group IV have an $IC_{50}$ of greater than 200 $\mu$M. The compounds of Group III have an $IC_{50}$ concentration of from between 100 $\mu$M and 200 $\mu$M and are the preferred compounds of the invention. The compounds of Group II have an $IC_{50}$ concentration of from between 10 $\mu$M and 99 $\mu$M and are the more preferred compounds of the invention. The compounds of Group I have an $IC_{50}$ concentration of <10 $\mu$M and are the most preferred compounds of the invention.

TABLE 1

Enzyme inhibition assay results for structures having the peptide backbone:
(Assay procedure described in Examples)

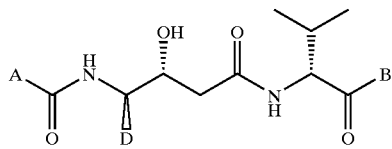

| Example | IC$_{50}$ Grouping | A | B |
|---|---|---|---|

Examples 1–16 D = 1-(2-methylpropyl)-

| 1 | II diastereomer I | 1-naphthyl-CH(OH)- | -NH-CH$_2$-C$_6$H$_4$-CO$_2$H |
| 2 | II diastereomer II | 1-naphthyl-CH(OH)- | -NH-CH$_2$-C$_6$H$_4$-CO$_2$H |
| 3 | III | 1-naphthyl-CH(OH)- | -NH-CH$_2$CH$_2$-C$_6$H$_4$-CO$_2$H |
| 4 | IV | 1-naphthyl-CH(OH)- | -NH-CH$_2$CH$_2$CH$_2$-CO$_2$H |
| 5 | IV | 1-naphthyl-CH(OH)- | -NH-CH$_2$-(1-naphthyl)-CO$_2$H |
| 6 | I | 1-naphthyl-CH(OH)- | -NH-cyclohexyl(CO$_2$H)(CO$_2$H) |
| 7 | II | 1-naphthyl-CH(OH)- | -NH-cyclohexyl-CO$_2$H |

TABLE 1-continued

Enzyme inhibition assay results for structures having the peptide backbone:
(Assay procedure described in Examples)

| Example | IC$_{50}$ Grouping | A | B |
|---|---|---|---|
| 8 | IV | 1-naphthyl-CH(OH)– | —OH |
| 9 | III | 1-naphthyl-CH(OBn)– | –NH-CH$_2$-C$_6$H$_4$-CO$_2$H |
| 10 | nd | PhCH(CH$_2$OH)– | –NH-CH$_2$-C$_6$H$_4$-CO$_2$H |
| 11 | II | 2-Br-C$_6$H$_4$-CH(OH)– | –NH-CH$_2$-C$_6$H$_4$-CO$_2$H |
| 12 | IV | PhCH$_2$-CH(OH)– | –NH-CH$_2$-C$_6$H$_4$-CO$_2$H |
| 13 | II | 3-(PhO)-C$_6$H$_4$-CH(OH)– | –NH-CH$_2$-C$_6$H$_4$-CO$_2$H |
| 14 | III | PhCH$_2$-CH(OH)– | –NH-CH$_2$-C$_6$H$_4$-CO$_2$H |
| 15 | IV | Ph-CH(OH)– | –NH-CH$_2$-C$_6$H$_4$-CO$_2$H |

TABLE 1-continued

Enzyme inhibition assay results for structures having the peptide backbone:
(Assay procedure described in Examples)

[Structure: A-C(=O)-NH-CH(D)-CH(OH)-C(=O)-NH-CH(iPr)-C(=O)-B]

| Example | IC$_{50}$ Grouping | A | B |
|---------|--------------------|---|---|
| 16 | IV | α-CF$_3$, α-OMe benzyl | 4-(CO$_2$H)benzylamino |
| 17 | III | (2S)-2-hydroxy-3-(methylthio)propyl | 4-(CO$_2$H)benzylamino |
| 18 | III diastereomer I | α-hydroxybenzyl | 4-(CO$_2$H)benzylamino |
| 19 | IV diastereomer II | α-hydroxybenzyl | 4-(CO$_2$H)benzylamino |

D = 4-methylbenzyl

| 20 | II | α-hydroxy-1-naphthylmethyl | 4-(CO$_2$H)benzylamino |

D = 2-thiophenylmethyl-

| 21 | I | α-hydroxy-1-naphthylmethyl | 3,4-di(CO$_2$H)cyclohexylamino |

D = 4-thiazolylmethyl-

| 22 | II | α-hydroxy-1-naphthylmethyl | 4-(CO$_2$H)benzylamino |

TABLE 1-continued
Enzyme inhibition assay results for structures having the peptide backbone:
(Assay procedure described in Examples)
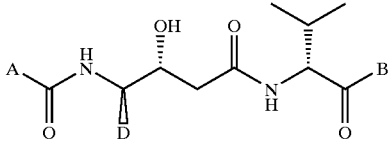
| Example | IC$_{50}$ Grouping | A | B |
|---------|---------|---|---|
| D = 3,5-difluorobenzyl- | | | |
| 23 | I | 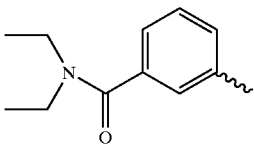 | 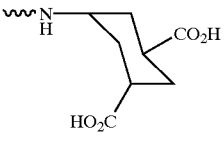 |
| 24 | II | 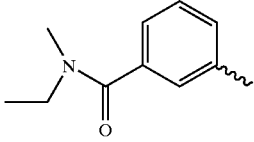 | —OH |
| 25 | I |  | 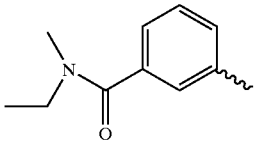 |
| 26 | I |  | —OH |
| 27 | I | 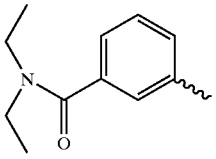 |  |
| 28 | I | 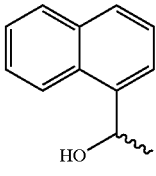 | 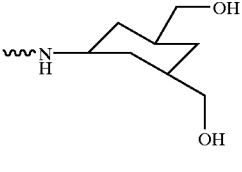 |
| 29 | I | 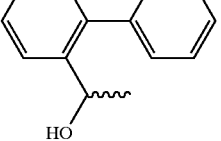 | Ala-Glu-Phe |
| 30 | II |  | Ala-Glu-Phe |

TABLE 1-continued

Enzyme inhibition assay results for structures having the peptide backbone:
(Assay procedure described in Examples)

| Example | IC$_{50}$ Grouping | A | B |
|---|---|---|---|
| 31 | I | N,N-dimethylamide-butyl | 4-amino-cyclohexane-1,3-dicarboxylic acid |
| 32 | II | N,N-dimethylamide-butyl | Ala-Glu-Phe |
| 33 | II | piperidinyl-butanoyl | Ala-Glu-Phe |
| 34 | II | morpholinyl-butanoyl | Ala-Glu-Phe |
| 35 | I | N-methyl-N-ethyl-benzamide | 4-amino-2,3-dimethoxy-cyclohexyl |
| 36 | I | 2,3-dihydro-1,4-benzodioxin-6-yl(hydroxy)methyl | 4-amino-cyclohexane-1,3-dicarboxylic acid |
| 37 | I | 3-carbamoyl-benzyl | 4-amino-cyclohexane-1,3-dicarboxylic acid |
| 38 | II | 3-acetamido-phenyl | 4-amino-cyclohexane-1,3-dicarboxylic acid |
| 39 | I | 3-(methoxycarbonyl)-benzyl | 4-amino-cyclohexane-1,3-dicarboxylic acid |

TABLE 1-continued

Enzyme inhibition assay results for structures having the peptide backbone:
(Assay procedure described in Examples)

| Example | IC$_{50}$ Grouping | A | B |
|---|---|---|---|
| 40 | I | 2-methoxy-benzyl alcohol (OMe, CH(OH)-) | 4-amino-cyclohexane-1,3-dicarboxylic acid |
| 41 | II | 4-methoxy-benzyl alcohol (MeO-, CH(OH)-) | 4-amino-cyclohexane-1,3-dicarboxylic acid |
| 42 | II | benzyl | 4-amino-cyclohexane-1,3-dicarboxylic acid |
| 43 | I | naphthyl | 4-amino-cyclohexane-1,3-dicarboxylic acid |
| 44 | II | cinnolinyl | Ala-Glu-Phe |
| 45 | II | 3-(4-methylpiperazin-1-yl-carbonyl)phenyl | 4-amino-cyclohexane-1,3-dicarboxylic acid |
| 46 | I | 3-(isobutyryl)phenyl | 4-amino-cyclohexane-1,3-dicarboxylic acid |
| 47 | I | 5-(N,N-dipropylcarbamoyl)-2,6-dimethylpyridin-3-yl | 4-amino-cyclohexane-1,3-dicarboxylic acid |

TABLE 1-continued
Enzyme inhibition assay results for structures having the peptide backbone:
(Assay procedure described in Examples)
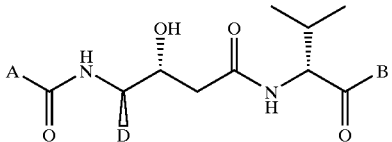
| Example | IC$_{50}$ Grouping | A | B |
|---|---|---|---|
| 47 | I | 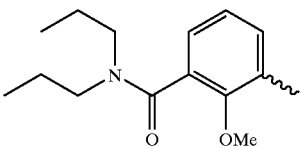 | 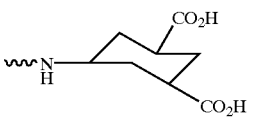 |
| 49 | I | 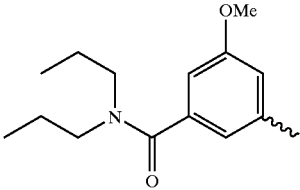 | 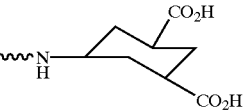 |
| 50 | I | 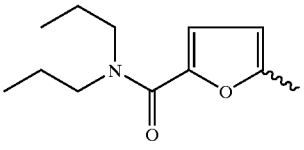 | 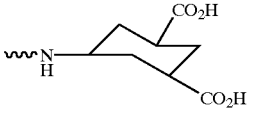 |
| 51 | I | 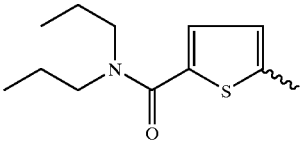 | 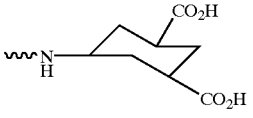 |
| 52 | I | 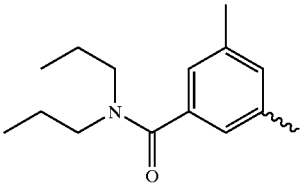 | 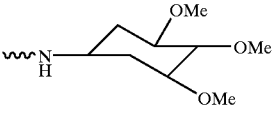 |
D = 3-trifluoromethylbenzyl-
| | | | |
|---|---|---|---|
| 53 | I | 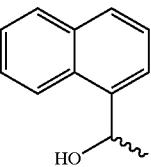 | 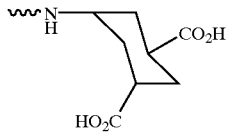 |

TABLE 1-continued

Enzyme inhibition assay results for structures having the peptide backbone:
(Assay procedure described in Examples)

| Example | IC$_{50}$ Grouping | A | B |
|---------|--------------------|---|---|

N,N- Di-n-propylcarboxamidobenzyl N-terminal group:

| 54 | I | | |

Scheme III illustrates the synthesis of aryl-substituted statine analogs via Weinreb amide formation and reduction followed by addition of a chiral enolate to give a diastereoselective product in a ratio of 7:1 of the desired isomer. This scheme can be generalized to make a variety of derivatized statine valine dimers with varying C- and N-terminal groups by selection of different stating materials and intermediates.

For example, the aryl statine derivative may be varied by selecting a different arylmethylene aminoacid as a starting material. All of the aryl amino acids used to form a derivatized aryl-statine were commercially available, and obtained from Synthetec, Inc. Monmouth Junction, N.J.

The following examples will serve to further illustrate preparation of the novel compounds of the invention.

Scheme III

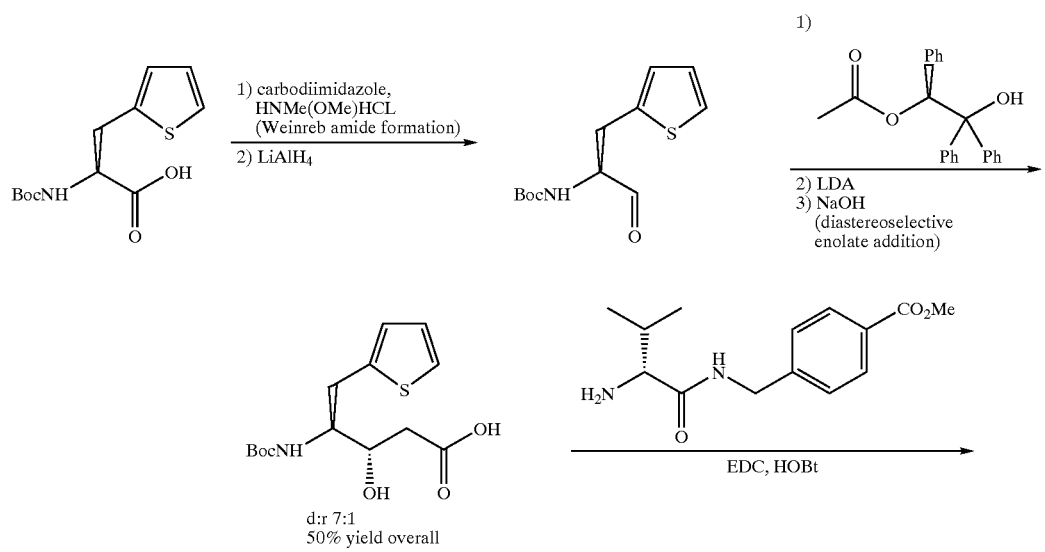

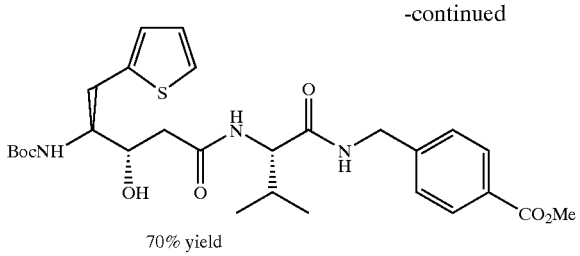

70% yield

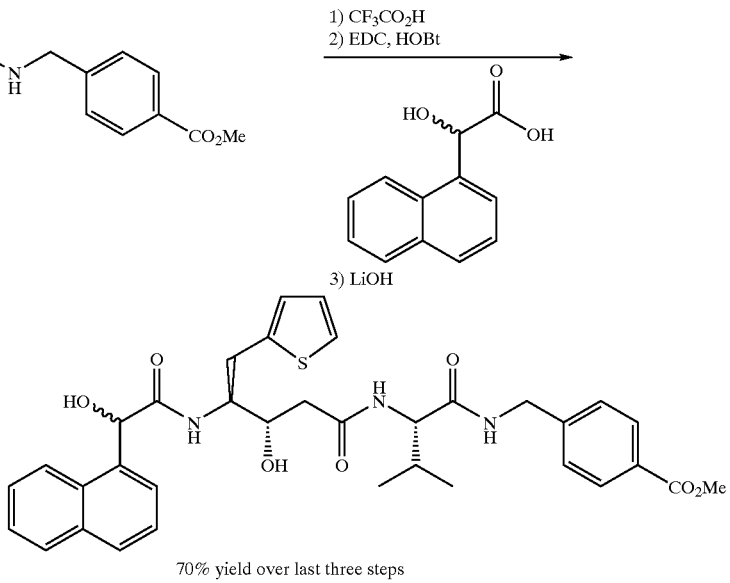

70% yield over last three steps

The invention is further illustrated by way of the following non-limiting examples.

EXAMPLE 1

Boc-Sta was coupled with carboxybenzylated valine using Step A, the Boc protecting group was removed as in Step B and the deprotected amine was coupled with (L)-1-naphthyl-hydroxyacetic acid according to Step C. The carboxybenzyl group was cleaved to the free acid using step E and then coupled with methyl 4-aminomethylbenzoate as described in step F. Finally the ester group on the C-terminal capping group was removed using Step G to provide the desired product. (L)-1-naphthyl-1-hydroxyacetic acid was obtained according to Scheme 2, reference 1 above, and then subjected to chiral separation to give an enhanced (L) isomer content.

| | |
|---|---|
| Molecular Formula | $C_{33}H_{41}N_3O_7$ |
| Molecular Weight | 591.70 |
| tlc Rf (solvent) | 0.1 (5% $MeOH/CH_2Cl_2$) |
| Purification: | Extraction (wash with EtOAc), Filtration (wash with $H_2O$) |
| H-nmr (solvent) | (DMSO): δ 8.529(t, 1H), 8.323(d, 1H), 7.932(m, 1H), 7.891, (d, 2H), 7.711(t, 2H), 7.516(m, 4H), 7.321(d, 2H), 5.639(s, 1H), 4.313(d, 2H), 4.157 (t, 1H), 3.893(m, 2H), 2.309(m, 2H), 1.990(m, 1H), 1.482(m, 2H), 1.306(m, 1H), 0.828(m, 12H) |
| Mass spec (MH+) | 592 |
| Synthetic Route Description | Method A, B, C, E, F, G Ref. 1 |

EXAMPLE 2

Boc-Sta was coupled with carboxybenzylated valine using Step A, the Boc protecting group was removed as in Step B and the deprotected amine was coupled with (D)-1-naphthyl-hydroxyacetic acid according to Step C. The carboxybenzyl group was cleaved to the free acid using step E and then coupled with methyl 4-aminomethylbenzoate as described in step F. Finally the ester group on the C-terminal capping group was removed using Step G to provide the desired product. (D)-1-naphthyl-1-hydroxyacetic acid was obtained according to Scheme 2, Refernce 1 above, and then subjected to chiral separation to give an enhanced (L) isomer content

| | |
|---|---|
| Molecular Formula | $C_{33}H_{41}N_3O_7$ |
| Molecular Weight | 591.70 |
| tlc Rf (solvent) | 0.1 (5% $MeOH/CH_2Cl_2$) |
| Purification: | Extraction (wash with EtOAc), Filtration (wash with $H_2O$) |
| H-nmr (solvent) | (DMSO): δ 8.539(m, 1H), 8.255(d, 1H), 7.805(m, 5H), 7.678,(m, 1H), 7.528(m, 4H), 7.349(d, 1H), 7.261(d, 1H), 6.578(d, 1H), 5.633(s, 1H), 5.110 (m, 1H), 4.314(d, 1H), 4.204(m, 2H), 3.936(m, 2H), 2.090(m, 1H), 1.544(m, 2H), 1.303(m, 1H), 0.838(m, 10H), 0.695(d, 2H) |
| Mass spec (MH+) | 592 |
| Synthetic Route Description | Method A, B, C, E, F, G Ref. 1 |

EXAMPLE 3

Boc-Sta was coupled with carboxybenzylated valine using Step A. The carboxybenzyl group was cleaved to the free acid using step E and then coupled with methyl 4-(2-aminoethyl-2-)benzoate as described in step F. The benzoate was prepared by reaction of methyl 2-bromoethyl-2-benzoate as in Step K with azide and then hydrogenation to the amine as in Step L. The N-terminal amine was coupled with (D)-1-naphthyl-hydroxyacetic acid according to Step C. The ester group on the C-terminal capping group was removed using Step G to provide the desired product

| | |
|---|---|
| Ex. 3: | 86570 |
| Molecular Formula | $C_{34}H_{43}N_3O_7$ |
| Molecular Weight | 605.72 |

| | |
|---|---|
| H-nmr (solvent) | (MeOD) δ 8.44(m, 1H); 8.0–7.2(m, 9H); 6.98(d, 1H); 5.80(m, 1H); 4.2–3.9(m, 3H); 3.5–3.2(m, 4H); 2.89–2.50(m, 4H); 2.1–1.3(m, 5H); 0.99(m, 12H); |
| C-nmr (solvent) | (MeOD) δ 174.182, 174.009, 173.884, 146.263, 146.138, 135.713, 131.010, 130.164, 130.086, 130.039, 129.992, 129.882, 129.803, 127.217, 127.060, 126.982, 126.888, 126.480, 126.339, 125.884, 125.775, 73.903, 73.762, 71.505, 60.344, 60.344, 60.375, 51.816, 41.893, 41.486, 41.313, 41.282, 36.187, 31.218, 26.014, 25.88, 23.662, 23.553, 22.157, 19.665, 19.207, 18.207, 17.98, 17.831 |
| Mass spec (MH+) | 606 |
| Synthetic Route Description | A, E, F, K, L, C, G |

EXAMPLE 4

Boc-Sta was coupled with carboxybenzylated valine using Step A, the Boc protecting group was removed as in Step B and the deprotected amine was coupled with 1-naphthyl-hydroxyacetic acid according to Step C. The carboxybenzyl group was cleaved to the free acid using step E and then coupled with methyl 4-aminobutanoate as described in step F. Finally the ester group on the C-terminal capping group was removed using Step G to provide the desired product.

| | |
|---|---|
| Molecular Formula | $C_{29}H_{41}N_3O_7$ |
| Molecular Weight | 544 |
| H-nmr (solvent) | (MeOD) δ 8.3–8.2(m, 2H); 7.8–7.6(m, 2H); 7.6–7.4(m, 3H); 6.34(d, 1H); 5.78(d, 1H); 4.1–3.9(m, 3H); 3.66(m, 2H); 3.2–3.0(m, 4H); 2.5–2.3(m, 3H); 2.01(m, 1H); 1.80–1.60(m, 3H); 1.33(m, 1H); 0.99(m, 12H) |
| C-nmr (solvent) | (MeOD) δ 177.113, 177.066, 175.655, 175.655, 175.483, 174.558, 137.861, 137.782, 135.698, 132.923, 132.782, 130.023, 129.850, 129.772, 127.358, 127.358, 127.078, 126.997, 126.888, 126.480, 126.884, 125.837, 125.355, 80.127, 73.950, 73.637, 71.646, 71.489, 71.411, 61.411, 61.551, 60.642, 60.375, 60.312, 53.290, 51.895, 51.675, 41.878, 41.564, 41.407, 41.188, 39.605, 32.127, 31.297, 26.011, 25.873, 25.669, 25.481, 23.662, 23.600 |
| Mass spec (MH+) | 545 |
| Synthetic Route Description | Method A, B, C, F, G |

EXAMPLE 5

The methyl ester of 4-aminomethylnaphthanlene-1-carboxylic acid (as synthesized by Steps O, K and L above) was coupled with the N-terminal capped dipeptide which was prepared as follows. Boc-Sta was coupled with carboxybenzylated valine using Step A, the Boc protecting group was removed as in Step B and the deprotected amine was coupled with 1-naphthyl-hydroxyacetic acid according to Step C. The carboxybenzyl group was cleaved to the free acid using step E. Finally the ester group on the C-terminal capping group was removed using Step G to provide the desired product.

| | |
|---|---|
| Molecular Formula | $C_{37}H_{43}N_3O_7$ |
| Molecular Weight | 641.75 |
| H-nmr (solvent) | (MeOD) δ 9.00(d, 1H); 9.0–7.2(m, 15H); 5.80(m, 1H); 4.90(m, 3H); 4.3–3.90(m, 4H); 2.5–2.0(m, 5H); 1.8–1.22(m, 5H); 0.99(m 12H) |
| C-nmr (solvent) | (MeOD) δ 175.60, 174.43, 174.04, 173.79, 171.156, 140.46, 140.35, 137.59, 135.71, 135.64, 133.02, 132.93, 132.72, 130.99, 130.95, 130.01, 129.82, 128.41, 127.78, 127.70, 127.59, 127.59, 127.123, 126.90, 126.84, 126.42, 126.36, 126.36, 126.25, 125.76, 125.54, 125.273, 124.98, 124.93, 73.92, 73.86, 73.62, 71.77, 71.66, 71.57, 71.46, 60.53, 60.49, 60.40, 52.85, 51.85, 42.10, 42.02, 41.99, 41.85, 41.78, 41.53, 31.56, 31.23, 25.97, 25.90, 25.86, 25.83, 23.69, 23.60, 23.52, 22.27, 22.21, 22.26, 22.16, 19.74, 19.68, 18.38, 18.14 |
| Mass spec (MH+) | 643 |
| Synthetic Route Description | A, E, F, G, K, L, O |

EXAMPLE 6

The dicarboxycyclohexane of this example was prepared as described above at step J was coupled with the N-terminal capped dipeptide which was prepared as follows. Boc-Sta was coupled with carboxybenzylated valine using Step A, the Boc protecting group was removed as in Step B and the deprotected amine was coupled with 1-naphthyl-hydroxyacetic acid according to Step C. The carboxybenzyl group was cleaved to the free acid using step E. Finally the ester groups on the C-terminal capping group were removed using Step G to provide the desired product

| | |
|---|---|
| Molecular Formula | C33H45N3O9 |
| Molecular Weight | 627 |
| tlc Rf (solvent) | Rf = 0.15 (10% MeOH/DCM) |
| Purification: | 1. Acid/Base Washes. |
| | 2. Trituration w/Ether/Filtration |
| Mass spec (MH+) | 628.2 (ESI -ppPositive) |
| Synthetic Route Description | Method A, B, E, J, F, G |
| | Method J: Amino-Aryl Diesters to Amino-Cyclohexyl Diesters |

EXAMPLE 7

The methyl aminocyclohexane-4-carboxylate of this example was coupled with the N-terminal capped dipeptide which was prepared as follows. Boc-Sta was coupled with carboxybenzylated valine using Step A, the Boc protecting group was removed as in Step B and the deprotected amine was coupled with 1-naphthyl-hydroxyacetic acid according to Step C. The carboxybenzyl group was cleaved to the free acid using step E. Finally the ester groups on the C-terminal capping group were removed using Step G to provide the desired product

| | |
|---|---|
| Molecular Formula | $C_{32}H_{45}N_3O_7$ |
| Molecular Weight | 583.33 |
| H-nmr (solvent) | (MeOD) δ 8.33(m, 2H); 7.88(m, 3H); 7.66–7.55(m, 3H); 5.88(s, 1H); 4.01–3.90(m, 3H); 3.76(m, 2H); 3.50(m, 1H); 3.33(m, 2H); 2.40–2.30(m, 3H); 2.1–1.9(m, 3H); 1.23(m, 1H); 0.99(m, 12H) |
| C-nmr (solvent) | (MeOD) δ 175.640, 174.182, 173.053, 137.782, 135.698, 135.729, 132.923, 130.054, 129.772, 127.421, 127.342, 127.123, 26.950, 126.370, |

| | |
|---|---|
| | 125.963, 125.775, 73.935, 71.693, 60.171, 52.412, 52.255, 41.721, 41.643, 32.080, 31.845, 30.121, 30.121, 29.995, 29.948, 29.870, 28.773, 26.343, 26.218, 26.067, 25.90, 23.537, 22.424, 22.283, 19.618, 19.571, 18.630, 18.270 |
| Mass spec (MH+) | 584 |
| Synthetic Route Description | Method A, B, C, G, F |

EXAMPLE 8

Boc-Sta was coupled with carboxybenzylated valine using Step A, the Boc protecting group was removed as in Step B and the deprotected amine was coupled with 1-naphthyl-hydroxyacetic acid according to Step C. The carboxybenzyl group was cleaved to the free acid using step E.

| | |
|---|---|
| Molecular Formula | $C_{25}H_{34}N_2O_6$ |
| Molecular Weight | 458.56 |
| H-nmr (solvent) | (MeOD) δ 8.33(m, 1H); 8.2–8.10(d, 2H); 7.77(m, 3H); 7.7–7.5(m, 3H); 5.88(d, 1H); 4.55(m, 1H); 4.2–3.9(m, 3H); 3.70(m, 1H); 2.46(m, 2H); 2.22(m, 1H); 1.66(m, 1H), 1.33(m, 1H); 0.99(m, 12H) |
| C-nmr (solvent) | (MeOD) δ 170.028, 169.871, 169.166, 169.119, 168.625, 168.555, 168.476, 168.476, 152.840, 131.584, 129.695, 126.695, 126.937, 126.842, 124.233, 123.888, 121.607, 121.043, 121.011, 120.502, 120.439, 119.945, 119.867, 74.283, 68.076, 67.934, 66.124, 65.818, 65.646, 53.200, 53.106, 47.682, 46.608, 46.514, 44.045, 35.604, 35.839, 25.541, 25.05, 22.97, 20.646, 19.668, 17.969, 16.433, 14.972, 13.698, 12.358, 12.287 |
| Mass spec (MH+) | 458 |
| Synthetic Route Description | Method A, B, G |

EXAMPLE 9

1-naphthyl-1-benzyloxyacetic acid was obtained according to Scheme 2, References 1 and 2 above. Boc-Sta was coupled with carboxybenzylated valine using Step A, the Boc protecting group was removed as in Step B and the deprotected amine was coupled with 1-naphthyl-benzyloxyacetic acid according to Step C. The carboxybenzyl group of the C-terminus was cleaved to the free acid using step E and then coupled with methyl 4-aminomethylbenzoate as described in step F. Finally the ester group on the C-terminal capping group was removed using Step G to provide the desired product.

| | |
|---|---|
| Molecular Formula | $C_{40}H_{47}N_3O_7$ |
| Molecular Weight | 681.85 |
| m.p. | |
| tlc Rf (solvent) | 0.3 (3% MeOH/CH$_2$Cl$_2$) |
| Purification: | Extraction (wash with EtOAc), Filtration (wash with H$_2$O) |
| H-nmr (solvent) | (DMSO): δ 8.58(m, 1H), 8.2(m, 1H), 7.94(m, 3H), 7.75(m, 2H), 7.33(m, 3H), 5.58(s, 1H), 4.62 (m, 2H), 4.33(m, 2H), 4.18(m, 1H), 3.93(m, 2H), 3.37(s, 2H), 2.36(m, 2H), 2.05(m, 1H), 1.57(m, 3H), 0.81(m, 12H) |
| Mass spec (MH+) | 680 |
| Synthetic Route Description | Methods: A, B, C, E, F, G, Ref. 1, Ref. 2 |

EXAMPLE 10

Boc-Sta was coupled with carboxybenzylated valine using Step A, the Boc protecting group was removed as in Step B and the deprotected amine was coupled with 2-phenyl-3-hydroxy-propionic acid according according to Step C. The carboxybenzyl group was cleaved to the free acid using step E and then coupled with methyl 4-aminomethylbenzoate as described in step F. Finally the ester group on the C-terminal capping group was removed using Step G to provide the desired product. (D)-1-naphthyl-hydroxyacetic acid was obtained according to Scheme 2, Reference 1 above, and then subjected to chiral separation to give an enhanced (L) isomer content

| | |
|---|---|
| Molecular Formula | $C_{30}H_{41}N_3O_7$ |
| Molecular Weight | 555.68 |
| tlc Rf (solvent) | 0.1 (3% MeOH/CH$_2$Cl$_2$) |
| Purification: | Extraction (wash with EtOAc), Filtration (wash with H$_2$O) |
| H-nmr (solvent) | (DMSO): δ 7.89(d, 2H), 7.69(m, 1H), 7.36(m, 5H), 4.34(m, 1H), 3.90(m, 1H), 3.80(m, 3H), 3.75 (m, 1H), 3.53(s, 2H), 2.10(m, 1H), 1.26(m, 1H), 0.89(m, 7H), 0.70(d, 2H), 0.58(d, 2H) |
| Mass spec (MH+) | 555 |
| Synthetic Route Description | Methods: A, B, C, E, F, G |

EXAMPLE 11

Boc-Sta was coupled with carboxybenzylated valine using Step A, the Boc protecting group was removed as in Step B and the deprotected amine was coupled with 2-bromomandelic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product. Bromomandelic acid was prepared from 2-bromophenylacetic acid in a manner analogous to Scheme 2.

| | |
|---|---|
| Molecular Formula | $C_{29}H_{38}N_3BrO_7$ |
| Molecular Weight | 620.55 |
| tlc Rf (solvent) | 0.1 (3% MeOH/CH$_2$Cl$_2$) |
| Purification: | Extraction (wash with EtOAc), Filtration (wash with H$_2$O) |
| H-nmr (solvent) | (DMSO): δ 8.56(m, 1H), 7.62(m, 2H), 7.56(m, 1H), 7.37(m, 3H), 7.22(m, 1H), 5.41(s, 1H), 5.33 (s, 1H), 4.33(m, 2H), 4.20(m, 1H), 3.92(m, 2H), 3.37(s, 2H), 2.28(m, 2H), 2.08(m, 1H), 1.52(m, 2H), 1.48(m, 1H), 0.89(m, 12H) |
| Mass spec (MH+) | 619 |
| Synthetic Route Description | Methods: A, B, C, E, F, G, Ref. 1 |

EXAMPLE 12

Boc-Sta was coupled with carboxybenzylated valine using Step A, the Boc protecting group was removed as in Step B and the deprotected amine was coupled with (D)-3-phenyl-2-hydroxy-propionic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{30}H_{41}N_3O_7$ |
| Molecular Weight | 555.69 |
| tlc Rf (solvent) | 0.1 (4% MeOH/$CH_2Cl_2$) |
| Purification: | Extraction (wash with EtOAc), Filtration (wash with $H_2O$) |
| H-nmr (solvent) | (DMSO): δ 8.62(t, 1H), 7.86(m, 6H) 7.36(d, 2H), 7.19(m,6H), 5.73(d, 1H), 4.96(d, 1H), 4.38(m, 2H), 4.29(m, 2H), 3.85(m, 3H), 2.97(m, 1H), 2.72 (m, 1H), 2.64(m, 4H), 2.24(m, 2H), 2.07(m, 1H), 1.32(m, 3H), 0.85(m, 12H) |
| Mass spec (MH+) | 554 |
| Synthetic Route Description | Methods: A, B, C, E, F, G |

EXAMPLE 13

Boc-Sta was coupled with carboxybenzylated valine using Step A, the Boc protecting group was removed as in Step B and the deprotected amine was coupled with 2-(3-benzoxyphenyl)-hydroxyacetic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product. 2-(3-benzoxyphenyl)-hydroxyacetic acid was prepared from 2-(3-benzoxyphenyl)-acetic acid by analogy to Scheme 2, Reference 1.

| | |
|---|---|
| Molecular Formula | $C_{35}H_{43}N_3O_8$ |
| Molecular Weight | 633.73 |
| tlc Rf (solvent) | 0.1 (2% MeOH/$CH_2Cl_2$) |
| Purification: | Extraction (wash with EtOAc), Filtration (wash with $H_2O$) |
| H-nmr (solvent) | (DMSO): δ 8.50(t, 1H), 7.89(m, 2H), 7.36(m, 5H), 7.15(m, 2H), 6.99(m, 3H), 4.98(m, 1.5H), 4.32(1.5H), 4.21(m, 1H), 3.8(m, 2H), 2.53(m, 2H), 2.3(d, 1H), 2.05(m, 1H), 1.5(m, 2H), 1.2 (m, 1H), 0.79(m, 12H) |
| Mass spec (MH+) | 632 |
| Synthetic Route Description | Methods: A, B, C, E, F, G, Ref. 1 |

EXAMPLE 14

Boc-Sta was coupled with carboxybenzylated valine using Step A, the Boc protecting group was removed as in Step B and the deprotected amine was coupled with (L)-3-phenyl-2-hydroxy-propionic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{30}H_{41}N_3O_7$ |
| Molecular Weight | 555.67 |
| tlc Rf (solvent) | 0.1 (2% MeOH/$CH_2Cl_2$) |
| Purification: | Extraction (wash with EtOAc), Filtration (wash with $H_2O$) |
| H-nmr (solvent) | (DMSO): δ 8.57(t, 1H), 7.88(d, 2H) 7.77(d, 1H), 7.39(d, 2H), 7.20(m, 6H), 4.36(m, 2H), 4.14(m, 1H), 3.88(m, 2H), 3.02(m, 1H), 2.73(m, 1H), 2.16 (d, 2H), 1.36(m, 2H) 1.24(m, 1H), 0.82(m, 12H) |
| Mass spec (MH+) | 554 |
| Synthetic Route Description | Methods: A, B, E, F, G |

EXAMPLE 15

Boc-Sta was coupled with carboxybenzylated valine using Step A, the Boc protecting group was removed as in Step B and the deprotected amine was coupled with 3-hydroxy-3-phenylpropionic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{30}H_{41}N_3O_7$ |
| Molecular Weight | 555.69 |
| tlc Rf (solvent) | 0.1 (3% MeOH/$CH_2Cl_2$) |
| Purification: | Extraction (wash with EtOAc), Filtration (wash with $H_2O$) |
| H-nmr (solvent) | (DMSO): δ 8.638(t, 1H), 8.283(m, 4H) 7.852(d, 2H), 7.75(d, 1H), 7.58(d, 1H), 7.35(d, 2H), 5.44 (m, 1H), 4.9(t, 1H), 4.8(m, 1H), 4.35(m, 2H), 4.2 (m, 1H), 3.8(m, 2H), 2.680(s, 1H), 2.586(d, 4H), 2.31(m, 3H), 2.11(m, 1H), 1.3(m, 1H), 1.1(m, 2H), 0.856(d, 6H), 0.737(d, 3H), 0.630(d, 3H) |
| Mass spec (MH+) | 556 |
| Synthetic Route Description | Methods: A, B, C, E, F, G |

EXAMPLE 16

Boc-Sta was coupled with carboxybenzylated valine using Step A, the Boc protecting group was removed as in Step B and the deprotected amine was coupled with 2-phenyl-2-tirfluoromehtyl-2-methoxy-acetic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{31}H_{40}N_3O_7F_3$ |
| Molecular Weight | 623.70 |
| tlc Rf (solvent) | 0.1 (3% MeOH/$CH_2Cl_2$) |
| Purification: | Extraction (wash with EtOAc), Filtration (wash with $H_2O$) |
| H-nmr (solvent) | (DMSO): δ 8.56(t, 1H), 7.88(m, 4H), 7.55(d, 2H), 7.41(m, 5H), 4.34(d, 2H), 4.19(t, 1H), 3.94(m, 2H), 3.38(s, 3H), 2.59(m, 3H), 2.15(d, 2H), 1.99 (m, 1H), 1.53(m, 2H), 1.30(m, 1H), 0.86(m, 12H) |
| Mass spec (MH+) | 622 |
| Synthetic Route Description | Methods: A, B, C, E, F, G |

EXAMPLE 17

Boc-Sta was coupled with carboxybenzylated valine using Step A, the Boc protecting group was removed as in Step B and the deprotected amine was coupled with 4-methylthio-2-hydroxy-butanoic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{26}H_{41}N_3O_7S$ |
| Molecular Weight | 539.69 |
| tlc Rf (solvent) | 0.1 (2% MeOH/CH$_2$Cl$_2$) |
| Purification: | Extraction (wash with EtOAc), Filtration (wash with H$_2$O) |
| H-nmr (solvent) | (DMSO): δ 8.60(m, 1H), 8.15(d, 2H) 7.32(d, 2H), 7.17(m, 1H), 4.34(m, 2H), 3.87(m, 1H), 2.52(m, 1H), 2.01(m, 1H), 1.25(m, 2H), 1.22(m, 1H), 1.05 (d, 1H), 0.86(m, 12H) |
| Mass spec (MH+) | 538 |
| Synthetic Route Description | Methods: A, B, C, E, F, G, Ref. 1 |

EXAMPLE 18

Boc-Sta was coupled with carboxybenzylated valine using Step A, the Boc protecting group was removed as in Step B and the deprotected amine was coupled with (D)-madelic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{29}H_{39}N_3O_7$ |
| Molecular Weight | 541.65 |
| tlc Rf (solvent) | 0.1 5% MeOH/CH$_2$Cl$_2$ |
| Purification: | Extraction (wash with EtOAc), Filtration (Wash with H$_2$O) |
| H-nmr (solvent) | (DMSO): δ 8.559(m, 1H), 7.868(m, 2H), 7.358(d, 1H), 7.317(m, 6H), 4.962(m, 1H), 4.162(m, 2H), 2.549(m, 8H), 2.290(m, 2H), 2.189(m, 1H), 1.461 (m, 2H), 1.238(m, 2H), 0.804(m, 12H) |
| Mass spec (MH+) | 542 |
| Synthetic Route Description | Method A, B, C, E, F, G |

EXAMPLE 19

Boc-Sta was coupled with carboxybenzylated valine using Step A, the Boc protecting group was removed as in Step B and the deprotected amine was coupled with (L)-madelic acid according to Step C. The carboxybenzyl group was cleaved to the free acid using step E and then coupled with methyl 4-aminomethylbenzoate as described in step F. Finally, the ester group on the C-terminal capping group was removed using Step G to provide the desired product.

| | |
|---|---|
| Molecular Formula | $C_{29}H_{39}N_3O_7$ |
| Molecular Weight | 541.65 |
| tlc Rf (solvent) | 0.1 5% MeOH/CH$_2$Cl$_2$ |
| Purification: | Extraction (wash with EtOAc), Filtration (Wash with H$_2$O) |
| H-nmr (solvent) | (DMSO): δ 8.535(m, 1H), 7.849(d, 2H), 7.418(d, 2H), 7.281(m, 5H), 4.963(m, 1H), 4.307(d, 2H), 4.162(m, 1H), 3.827(m, 2H), 2.509(m, 3H), 2.266 (m, 1H), 2.189(m, 1H), 1.461(m, 2H), 1.336(m, 3H), 0.826(m, 12H) |
| Mass spec (MH+) | 542 |
| Synthetic Route Description | Method A, B, C, E, F, G |

EXAMPLE 20

The 4-methylbenzyl statine derivative was prepared according to the procedure of Wuts given above. The dipeptide was prepared as in Examples 1 or 2 with the exception that the Boc-statine derivative was substituted for Boc-statine.

| | |
|---|---|
| Molecular Formula | C37 H41 N3 O7 |
| Molecular Weight | 639 |
| tlc Rf solvent | 0.2 (10% MeOH/CH2Cl2) |
| Purification: | Flash chromatography |
| H-nmr (solvent) | (1:1 CD3OD:CDCl3) δ 8.31–6.70(m, 15H, Ar—H), 5.72(s, CH, 0.33H), 5.57(s, CH, 0.67H), 4.40–3.90(m, 5H), 3.00–2.70(m, 2H), 2.55–1.80 (m, 2H), 2.28(s, 1H), 2.23Y(s, 2H), 0.90(d, J=6.8Hz, 1H), 0.86(d, J=6.8Hz, 1H), 0.72(d, J=6.8Hz, 2H), 0.53(d, J=6.8Hz, 2H), |
| C-nmr (solvent) | (1:1 CD3OD:CDCl3) δ 174.6, 174.5, 173.1, 172.9, 172.81, 172.77, 169.4, 144.3, 144.2, 136.5, 136.3, 135.9, 135.4, 135.3, 134.7, 134.4, 132.0, 131.7, 130.44, 130.39, 129.7, 129.6, 129.5, 129.4, 129.3, 129.2, 129.1, 127.81, 127.78, 126.70, 126.66, 126.4, 126.3, 126.1, 125.9, 125.7, 125.6, 124.9, 124.2, 72.9, 72.1, 70.1, 69.8, 59.7, 59.6, 54.4, 54.3, 43.2, 41.1, 41.0, 38.14, 38.09, 30.7, 30.5, 30.1, 21.2, 21.1, 19.5, 19.4, 17.9, 17.6 |
| Mass spec (MH+) | (CI) 640.3 |
| Synthetic Route Description | Wuts ref., A, B, C, G |

EXAMPLE 21

1-amino-3,5-cis,cis-dimethylcyclohexyldicarboxylate

To 10 g (47.85 mmole) of dimethyl-5-isophthalate in 25 ml of acetic acid and 50 ml of methanol was added 5 g of 5% rhodium in alumina in a high-pressure bottle, which was saturated with hydrogen at 55 psi and shaken for one week of time. The mixture was then filtered through a thick layer of Celite cake and rinsed with methanol three times, the solvent was concentrated and the crude solid was triturated with diethyl ether and filtered again, it afforded 9.67 g (44.98 mmole) of 1-amino-3,5-cis,cis-dimethyl cyclohexyldicarboxylate, a pale-white solid at 94% yield, reverse phase HPLC has shown a purity of 94.4%.

The 2-thiophenylmethyl statine derivative was prepared according to the procedure of Wuts given above. The dipeptide was prepared as in Examples 1 or 2 with the exception that the Boc-statine derivative was substituted for Boc-statine.

| | |
|---|---|
| Molecular Formula | C34 H41 N3 O9 S |
| Molecular Weight | 667 |
| tlc Rf (solvent) | 0.2 (20% MeOH/CH2Cl2) |
| Purification: | Flash chromatography and HPLC |
| H-nmr (solvent) | (1:1 CD3OD:CDCl3) δ 8.30–6.70(m, 10H), 5.77(s, 0.5H), 5.68(s, 0.5H), 4.30–3.80(m, 3H), 3.80–3.60(m, 1H), 3.20–2.90(m, 2H), 2.50–1.80 (m, 5H), 1.50–1.00(m, 4H), 1.00–0.50(m 6H). |
| C-nmr (solvent) | (1:1 CD3OD:CDCl3) δ 177.54, 177.47, 177.41, 177.33, 177.30, 17.97, 174.89, 173.2, 173.1, 172.8, 172.1, 172.0, 140.8, 140.7, 136.8, 136.1, 134.8, 134.7, 132.2, 132.0, 129.7, 129.6, 129.3, 127.6, 127.57, 127.5, 127.4, 127.1, 126.92, 126.88, 126.6, 126.55, 126.47, 127.4, 127.1, 126.9, 126.88, 126.6, 126.5, 126.47, 126.39, 126.32, 126.24, 126.16, 126.0, 125.94, 125.86, 125.2, 124.7, 124.6, 124.5, 72.9, 72.3, 69.7, 69.6, 59.5, 59.4 54.8, 54.6, 41.1, 41.0, 34.5, 34.4, 34.3, 32.5, 32.3, 31.2, 31.0, 30.83, 30.76, 19.4, 19.3, 18.1, 18.0, 17.9, 17.5. |
| Synthetic Route Description | Wuts ref., A, B, C, G |

EXAMPLE 22

The 4-thiazolylmethyl statine derivative was prepared according to the procedure of Wuts given above. The dipeptide was prepared as in Examples 1 or 2 with the exception that the Boc-statine derivative was substituted for Boc-statine.

| | |
|---|---|
| Molecular Formula | C34 H36 N4 O7 S |
| tlc Rf solvent | 0.6 (20% MeOH/CH2Cl2) |
| Purification: | Flash chromatography |
| Synthetic Route Description | Wuts ref., A, B, C, G |
| tlc Rf (solvent) | 0.6 (20% MeOH/CH2Cl2) |
| Purification: | Flash chromatography |
| H-nmr (solvent) | (1:1 CD3OD:CDCl3) δ 8.66(d, J=1.9Hz, 1H), 8.47(t, J=5.9Hz, 0.5H), 8.34(t, J=5.9Hz, 0.5H), 8.30–8.05(m, 1H), 8.00–7.00(m, 9H), 6.90–6.80 (m, 1H), 5.75(s, 0.5H), 5.61(s, 0.5H), 4.50–4.00 (m, 5H), 3.20–3.00(m, 2H), 2.55–2.20(m, 2H), 2.20–1.80(m, 1H), 0.90(t, J=7.5Hz, 3H), 0.75(d, J=6.8Hz, 1.5H), 0.58(d, J=6.8Hz, 1.5H). |
| C-nmr (solvent) | (1:1 CD3OD:CDCl3) δ 174.5, 172.8, 172.7, 172.5, 169.2, 153.9, 153.71, 153.67, 144.25, 144.21, 136.3, 136.1, 134.6, 134.5, 131.8, 131.6, 130.4, 130.3, 129.9, 129.8, 129.5, 129.3, 129.2, 129.1, 127.8, 127.7, 126.7, 126.6, 126.3, 126.2, 125.7, 125.6, 125.5, 124.8, 124.4, 115.8, 115.7, 78.2, 72.9, 72.3, 70.0, 59.6, 59.5, 52.7, 52.5, 43.1, 40.9, 40.8, 33.8, 30.7, 30.5, 19.5, 19.4, 17.9, 17.7 |
| Mass sec (MH+) | (CI) 633.2 |

General Procedures for Preparing C-terminal Benzamides

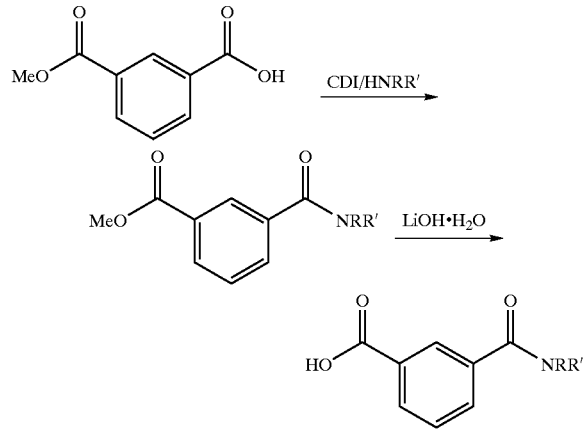

Methyl isophthalate (1 equiv, 11.1 mmol) was dissolved in 50:50 THF:DMF (20 mL) before the addition of 1,1' carbonyldiimidazole (CDI) (1.2 equiv, 13.3 mmol) at ambient temperature. Upon addition of CDI, a color change from colorless to yellow, as well as evolution of gas ($CO_2$), were observed. After gas evolution subsided (approximately one minute or less), the amine (1.2 equiv, 13.3 mmol) was added. After 12 h of stirring at ambient temperature, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave the crude white solid or clear oil. Purification of these compounds if needed was achieved via chromatography on silica gel with 30–40% ethyl acetate in hexanes. (80–90% yield)

The methyl isophthalate mono-alkyl or di-alkyl amide was then treated with LiOH.H$_2$O (3 equiv, 33.3 mmol) in a minimum amount of 1:2:1 THF:MeOH:H$_2$O and allowed to stir overnight at ambient temperature. After 12 h, the solvents were removed in vacuo and subsequently partitioned between H$_2$O and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated HCl until pH~3. The cloudy-white acidic aqueous solution thus obtained was then extracted three times with ethyl acetate. These combined organic extracts were dried over anhydrous $MgSO_4$ or $NaSO_4$. Filtration of the drying agent and removal of solvents in vacuo gave the crude white solid. The mono- or di-alkyl amide isophthalate was used crude in the next reaction. (90–100% yield)

Using the procedure above with following materials, the corresponding mono-amides can be prepared for coupling as N-terminal capping groups to the dipeptides: 5-methyoxy-1,3-benzenedicarboxylic acid (Ubichem); chelidonic acid; (Aldrich or Fluka); furan-2,5-dicarboxylic acid (Apin Chemical or Salor); 3,5-dicarboxy-1,4-dioxacyclohexa-2,5-diene (Maybridge Chemical, Maybridge NRB02029); 3,5-pyrrazoledicarboxylic acid (ICN Chemicals); 3,5-pyridinedicarboxylic acid (Aldrich Chemicals).

General Procedure 2

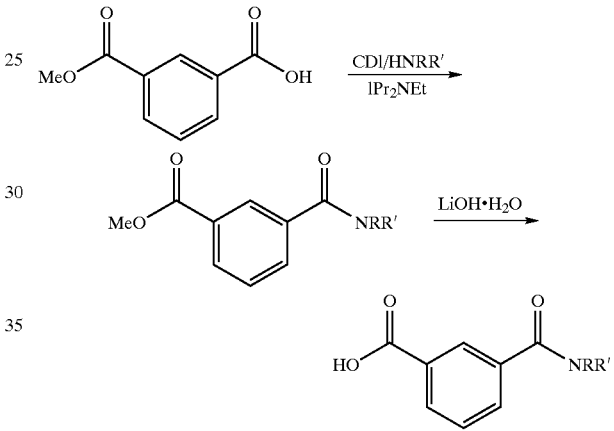

Methyl isophthalate (1 equiv, 11.1 mmol) was dissolved in 50:50 THF:DMF (20 mL) before the addition of 1,1' carbonyldiimidazole (CDI) (1.2 equiv, 13.3 mmol) at ambient temperature. Upon addition of CDI, a color change from colorless to yellow, as well as evolution of gas ($CO_2$), were observed. After gas evolution subsided (approximately one minute or less), the amine (1.2 equiv, 13.3 mmol) dissolved in DMF and diisopropylethyl amine (1.2 equiv, 13.3 mmol) was added. After 12 h of stirring at ambient temperature, the reaction was partitioned between saturated aqueous $NH_4Cl$ and ethyl acetate, and the aqueous layer was extracted twice more with ethyl acetate. The organic extracts were then washed with saturated aqueous solutions of $NaHCO_3$ and NaCl, and dried over anhydrous $MgSO_4$ or $NaSO_4$. Filtration of the drying agent and removal of solvents in vacuo gave the crude white solid or clear oil. Purification of these compounds if needed was achieved via chromatography on silica gel with 30–40% ethyl acetate in hexanes. (80–90% yield)

The methyl isophthalate mono-alkyl or di-alkyl amide (1 equiv, 11.1 mmol) was then treated with LiOH.H$_2$O (3 equiv, 33.3 mmol) in a minimum amount of 1:2:1 THF:MeOH:H$_2$O and allowed to stir overnight at ambient temperature. After 12 h, the solvents were removed in vacuo and subsequently partitioned between H$_2$O and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated HCl until pH~3. The cloudy-white acidic aqueous solution thus obtained was then extracted three times with ethyl acetate. These combined organic extracts were dried over anhydrous $MgSO_4$ or $NaSO_4$. Filtration of the drying agent and removal of solvents in vacuo gave the crude white solid. The mono- or di-alkyl amide isophthalate was used crude in the next reaction. (90–100% yield)

EXAMPLE 23

The 3,5-difluorobenzylstatine (3,5-difluoroPhe/Sta) derivative was prepared according to the procedure of Wuts given above. The dipeptide was prepared as in Examples 1 or 2 with the exception that the Boc-statine derivative was substituted for Boc-statine.

| | |
|---|---|
| Molecular Formula | $C_{36}H_{46}F_2N_4O_9$ |
| Molecular Weight | 716.77 |
| m.p. | |
| tlc Rf (solvent) | |
| Purification: | |
| H-nmr (solvent) | ($CD_3OD$) δ 7.9 (m, 1H, aryl), 7.8(s, 1H, aryl), 7.5 (m, 2H, aryl), 6.9(d, 2H, aryl), 6.7(m, 1H, aryl), 4.4(m, 1H), 4.2–4.0(m, 2H), 3.9–3.7(m, 1H), 3.6–3.5(m, 2H, N–CH$_2$), 3.3–3.2 (m, 2H, N–CH$_2$), 3.1–3.0(m, 2H), 2.6–2.4(m, 4H), 2.3–2.0(m, 4H), 1.4–1.0(m, 7H), 0.98–0.81(m, 6H, CH$_3$ × 2) |
| C-nmr (solvent) | ($CD_3OD$) δ 172.06, 168.11, 167.14, 163.53, 160.24, 160.08, 156.97, 156.79, 138.77, 138.65, 132.41, 130.25, 124.342, 124.10, 123.64, 120.35, 107.41, 107.09, 96.92, 96.58, 96.24, 64.72, 54.48, 50.03, 38.94, 36.38, 35.49, 34.93, 32.03, 29.33, 25.83, 25.57, 13.57, 12.30, 8.27, 6.97 |
| IR (solvent/bulk medium) | |
| Mass spec (M+Na+) | (M+Na$^+$) 739.4 |
| Elemental Analysis-Calc (%) | |

EXAMPLE 24

This example was prepared as in Example 23, but the C-terminal carboxyl group was not coupled with an amino bearing substituent.

| | |
|---|---|
| Molecular Formula | C27H33F2N3O6 |
| Molecular Weight | 533 |
| tlc Rf (solvent) | Rf = 0.52 (10% MEOH/DCM) |
| Purification: | 1. Acid/Base Washes |
| | 2. Trituration/Filtration |
| H-nmr (solvent) | (CD3OD) δ N/A |
| C-nmr (solvent) | (CD3OD) δ N/A |
| Mass spec (MH+) | 534.3 (M+ H, APCI-positive mode) |
| | 556.3 (M+ Na) |
| | 572.1 (M+ K) |
| Synthetic Route Description | Procedure Q-EDC Coupling |

EXAMPLE 25

Starting material for the N-terminal groups was obtained by the procedures outlined in Example 23 above. The C-terminal was obtained by coupling Boc-Val with ethylamine

| | |
|---|---|
| Molecular Formula | C29H38F2N4O5 |
| Molecular Weight | 560 |
| tlc Rf (solvent) | Rf = 0.39 (10% MEOH/DCM) |
| Purification: | 1. Acid/Base Washes |
| | 2. Trituration/Filtration |
| H-nmr (solvent) | (CD3OD) δ 7.86(d, ArH, J=1.7, 1H), 7.8(m, ArH, 1H), 7.53(d, ArH, J=5.5, 2H), 6.91(d, ArH, J=6.6, 2H), 6.72(t, ArH, J=2.2, 2.7, 1H), 4.4(m, CH, 1H), 3.6(m, OH, 1H), 3.2(m, CH2, 2H), 3.0(m, CH2, CH2, 4H), 2.49(t, CH2, J=6.0, 6.6, 2H), 2.11(t, CH, J=6.0, 6.6, 1H), 1.24(dt, CH3, J=3.3, 7.1, 7.7, 5.0, 3H), 1.1(m, CH3, CH3, 6H), 0.9(m, (CH3)2, 6H). |
| C-nmr (solvent) | (CD3OD) δ 174.1, 138.1, 130.1, 113.4, 113.1, 102.5, 71.0, 60.5, 60.4, 56.0, 41.5, 38.3, 35.2, 31.4, 19.6, 18.3, 18.2, 14.8, 14.7. |
| Mass spec (MH+) | 561.1 (M+ H, APCI-positive mode) |
| | 583.1 (M+ Na) |
| Synthetic Route Description | Procedure Q-EDC Coupling |

EXAMPLE 26

The compound was made as in Example 24, except that the diethylbenzamide was prepared according to the General Procedure for preparing benzamides given above and coupled with the 3,5-difluoroPhe/Sta dipeptide.

EXAMPLE 27

1-amino-3,5-cis,cis-dihydroxymethylenecyclohexane

The dimethyl 3,5-dicarboxycyclohexane as prepared in Example 23 was reduced using LiAlH4 to provide the title compound above, which was subsequently coupled to the C-terminal end of the dipeptide using standard EDC coupling.

| | |
|---|---|
| Molecular Formula | C36H45F2N3O7 |
| Molecular Weight | 669 |
| tlc Rf (solvent) | Rf = 0.33 (10% MEOH/DCM) |
| Purification: | 1. Acid/Base Washes |
| | 2. Trituration/Filtration |
| Mass spec (MH+) | 669.1 (M+ H, APCI-positive mode) |
| Synthetic Route Description | Procedure Q-EDC Coupling |

EXAMPLE 28

General procedure for preparation of biphenyl N-terminal groups is illustrated by the preparation with α-hydroxy-α-(2-biphenyl)acetic acid:

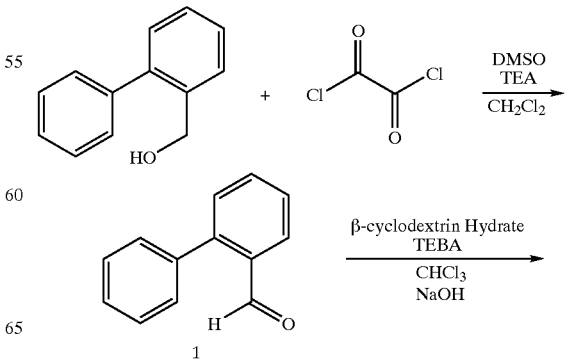

1

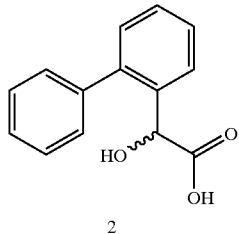

A solution of CH$_2$Cl$_2$ (25 mL) and oxalyl chloride(2 mL, 21.16 mmol) was placed in a 100-mL round bottom flask kept under nitrogen. The oxalyl chloride solution was stirred at −50 to −60° C. Me$_2$SO (2.5 mL, 35.82 mmol) was dissolved in CH$_2$Cl$_2$ (5mL). The Me$_2$SO was added dropwise to the stirred oxalyl chloride solution at −50 to −60° C. The reaction mixture was stirred for 2 min and the alcohol (16.28 mmol in 10 mL CH$_2$Cl$_2$) was added within 5 min; stirring was continued for an additional 60 min. TEA (11.30 ml, 81.4 mmol) was added and the reaction mixture was stirred for 60 min and then allowed to warm to room temperature. Water (60 mL) was then added and the aqueous layer was reextracted with additional CH$_2$Cl$_2$ (60 mL). The organic layers were combined, washed with saturated NaCl solution (120 mL), and dried over anhydrous MgSO$_4$. The filtered solution was concentrated in a rotary evaporator to dryness. The oil was chromatographed on silica gel (98:2 hexanes: ETOAc) to give Compound 1, 2.5 g (86%).

A mixture of 5.46 mmol of aromatic aldehyde(compound 1) in 10 mL of CHCl$_3$ and β-cyclodextrins (CDs) (0.11 mmol) and triethylbenzylammonia chloride(TEBA)(0.273 mmol)in a flask equipped with a magnetic stirrer and dropping funnel was stirred for 20 minute at 50° C. Then 10 g of sodium hydroxide dissolved in 10 mL of water was added dropwise to the flask with stirring. After completion of the addition, the reaction was continued for 8 h with the temperature maintained at 50° C. Then enough of distilled water was added to dissolve the precipitate formed during the reaction, and the resulting solution was thoroughly washed with ether, adjusted to pH 3 with dilute hydrochloric acid and extracted with 3×30 mL of ether. The extract was dried with anhydrous sodium sulfate, then evaporated to dryness and the remaining precipitate was subjected to column chromatography on silica gel using DCM:MeOH:AcOH (95:5:1) to give compound 2 (30%).

| | |
|---|---|
| Molecular Formula | C29H38F2N4O5 |
| Molecular Weight | 581 |
| tlc Rf (solvent) | Rf = 0.52/0.5 (10% MEOH/DCM) |
| Purification: | 1. Acid Base Washes |
| | 2. Trituration/Filtration |
| H-nmr (solvent) | (CD3OD) δ 7.3(m, ArH, 9H), 6.96(d, NH, J=6.6, 1H), 6.84(d, NH, J=6.1, 1H), 6.75(t, NH, J=9.9, 6.6, 1H), 5.1(m, OH, CH, 2H), 4.1(m, OH, CH, CH, 3H), 3.2(m, CH2, 2H), 2.9(m, CH2, 2H), 2.4(m, CH2, 2H), 2.1(m, CH, 1H), 1.1(m, CH3, 3H), 0.9(m, (CH3)2, 6H). |
| C-nmr (solvent) | (CD3OD) δ 175.9, 174.3, 143.9, 131.3, 131.0, 129.2, 129.1, 128.8, 128.4, 128.2, 113.7, 113.5, 113.4, 113.1, 71.5, 70.9, 70.1, 60.5, 60.4, 60.3, 55.2, 55.1, 54.7, 41.8, 41.4, 38.6, 35.2, 31.5, 31.4, 19.6, 18.3, 18.1, 14.7, 14.6. |
| Mass spec (MH+) | 582.3 (M+ H, APC-positive mode) |
| | 604.3 (M+ Na) |
| | 620.1 (M+ K) |
| Synthetic Route Description | Procedure Q-EDC Coupling |

EXAMPLE 29

This test compound was prepared by coupling commercially available 2-carboxy-diphenylether with the peptide 3,5-difluoroPhe/Sta-Val-Ala-Glu-Phe [SEQ ID NO:1] according to the standard EDC coupling procedures. The VAEF [SEQ ID NO:2] peptide sequence was previously established to possess inhibitory binding capability at the active site of the enzyme.

EXAMPLE 30

This test compound was prepared by analogy to Example 29 using 2-carboxy-diphenylketone.

EXAMPLE 31

Dimethyl-4-carboxamidobutanoic acid was prepared by aminolysis of glutaric anhydride with dimethylamine and was then coupled to the C-terminal functionalized didpeptide by standard EDC coupling.

EXAMPLE 32

The geminal dimethyl analog of 32 was prepared as in Example 31, but using the 3,3-demethylglutaric anhydride. This groups was coupled to the derivatized Sta-Val-Ala-Glu-Phe [SEQ ID NO:3] pentapeptide and assayed for binding affinity in the enzyme system.

EXAMPLE 33

Glutaric anhydride was treated with methanol to provide the mono methyl ester, which was treated with phosgene to produce the mono methyl ester with the opposite end being the acid chloride. The acid chloride was treated with piperidine to form the amide. The methyl ester was then hydrolyzed to the free acid and coupled with the derivatized Sta-Val-Ala-Glu-Phe [SEQ ID NO:3] pentapeptide.

EXAMPLE 34

The procedure of Example 33 was used except that morpholine was added to the acid chloride to produce the morpholino amide.

EXAMPLE 35

1-amino-3,5-cis,cis-dimethoxy cyclohexane

To 10 g (65.36 mmole) of 3,5-dimethoxyaniline was reduced as described in the procedure of Example 21 for the cyclohexyldicarboxylate and afforded 7.78 g (48.92 mmole) of as 1-amino-3,5-cis,cis-dimethoxy cyclohexane, a pale yellow solid at 75% yield.

| | |
|---|---|
| Molecular Formula | C34H46F2N4O7 |
| Molecular Weight | 660 |
| tlc Rf (solvent) | Rf = 0.3 (10% MEOH/DCM) |
| Purification: | 1. Acid/Base Washes |
| | 2. Trituration/Filtration |
| H-nmr (solvent) | (CD3OD) 7.9(m, ArH, 1H), 7.8(m, ArH, 1H), 7.5(m, ArH, 2H), 6.9(m, ArH, 2H), 6.7(m, ArH, 1H), 4.4(m, CH, 1H), 4.2(m, CH, CH, 2H), 3.7(m, OH, 1H), 3.1(m, CH2, 2H), 2.9(m, CH2, 2H), 2.5(m, CH2, 2H), 2.1(m, CH, 1H), 1.2(m, CH2, CH2, CH2, 6H), 1.0(m, (CH3)2, 6H). |
| C-nmr (solvent) | (CD3OD) 174.1, 173.0, 136.2, 131.1, 130.0, 129.9, 127.1, 113.5, 113.2, 102.9, 102.6, 76.6, 70.8, 60.4, 56.4, 56.0, 45.1, 41.5, 39.9, 38.5, 38.4, 38.1, 35.6, 31.6, 19.6, 18.3. |
| Mass spec (MH+) | 661.4 (M+ H, APCI-positive mode) |
| | 683.4 (M+ Na) |
| Synthetic Route Description | Procedure Q-EDC Coupling |

EXAMPLE 36

| | |
|---|---|
| Molecular Formula | $C_{34}H_{41}F_2N_3O_{11}$ |
| Molecular Weight | 705.70 |
| H-nmr (solvent) | (CD$_3$OD) δ 8.40(m, 1H); 8.0–7.6(m, 2H); 6.9–6.6(m, 6H); 5.40(s; 1H); 4.2–4.0(m, 6H); 3.77(m, 1H); 3.33(m, 2H); 2.89(m, 2H); 2.6–2.0(m, 8H); 1.4–1.2(m, 4H); 0.99(m, 6H) |
| C-nmr (solvent) | (CD$_3$OD) δ 183.086; 178.101; 178.038; 177.975; 175.498; 174.009; 173.899; 173.069; 145.134; 144.946; 144.884; 144.241; 134.820; 132.531; 129.992; 120.505; 118.219; 118.094; 116.934; 116.871; 116.792; 113.406; 113.375; 113.077; 113.046; 103.107; 102.998; 102.763; 102.653; 102.308; 75.048; 74.797; 76.395; 70.282; 65.485; 60.265; 54.998; 54.450; 42.332; 41.580; 41.423; 40.122; 38.304; 35.325; 31.75; 42.364; 42.332; 41.580; 41.423; 40.122; 38.304; 35.325; 31.751; 31.688; 24.864; 19.619; 18.427; 18.301 |
| Mass spec (M+Na+) | 706 |

EXAMPLE 37

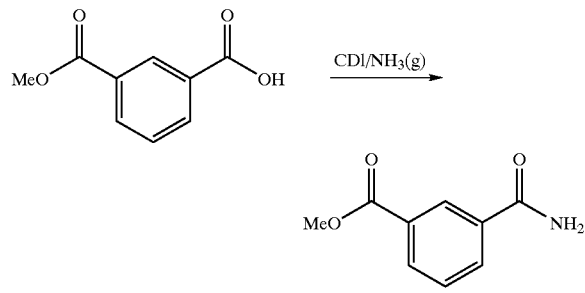

Methyl isophthalate (1 equiv, 11.1 mmol) was dissolved in 50:50 THF:DMF (20 mL) before the addition of 1,1' carbonyldiimidazole (CDI) (1.2 equiv, 13.3 mmol) at ambient temperature. Upon addition of CDI, a color change from colorless to yellow, as well as evolution of gas (CO$_2$), were observed. After five minutes, ammonia gas was bubbled into the solution through a syringe needle for 1 h. Since the reaction was heating up due to an exotherm, the reaction was cooled to 0° C. for the duration of the hour. The reaction was then left stirring under a balloon of ammonia overnight at ambient temperature. After 12 h, the reaction was partitioned between saturated aqueous NH$_4$Cl and ethyl acetate, and the aqueous layer was extracted twice more with ethyl acetate. The organic extracts were then washed with saturated aqueous solutions of NaHCO$_3$ and NaCl, and dried over anhydrous MgSO$_4$ or NaSO$_4$. Filtration of the drying agent and removal of solvents in vacuo gave the crude white solid or clear oil. Purification via chromatography on silica gel with 5% isopropanol in chloroform gave the desired primary amide. (65% yield)

The methyl isophthalate primary amide (7.26 mmol) was then treated with LiOH.H$_2$O (3 equiv, 21.8 mmol) in a minimum amount of 1:2:1 THF:MeOH:H$_2$O and allowed to stir overnight at ambient temperature. After 12 h, the solvents were removed in vacuo and subsequently partitioned between H$_2$O and ethyl acetate. The aqueous layer was extracted once more with ethyl acetate (to remove any unreacted starting material). The aqueous layer was then acidified with concentrated HCl until pH~3. The cloudy-white acidic aqueous solution thus obtained was then extracted three times with ethyl acetate. These combined organic extracts were dried over anhydrous MgSO$_4$ or NaSO$_4$. Filtration of the drying agent and removal of solvents in vacuo gave the crude white solid. The mono- or di-alkyl amide isophthalate was used crude in the next reaction. (90–100% yield)

EXAMPLE 38

2-carboxymethylaniline was treated with acetyl chloride to form the acylamino substituent. The methyl ester was then hydrolyzed to provide the free acid which was coupled using the standard EDC procedure.

| | |
|---|---|
| Molecular Formula | $C_{33}H_{40}F_2N_4O_9$ |
| Molecular Weight | 674.69 |
| H-nmr (solvent) | (CD$_3$OD) δ 7.90(s, 1H, aryl), 7.68(d, 1H, aryl), 7.47(d, 1H, aryl), 7.37(t, 1H, aryl), 6.91(d, 2H, aryl), 6.71(m, 1H, aryl), 4.40–4.35(m, 1H), 4.18–4.12(m, 2H), 3.82–3.71(m, 1H), 3.65(s, 6H, OCH$_3$ × 2), 3.1–2.95(m, 2H), 2.56–2.44(m, 4H), 2.18–2.07(m, 4H), 2.13(s, 3H, CH$_3$), 1.43–1.27 (m, 4H), 0.95–0.85(m, 6H, CH$_3$ × 2) |
| Mass spec (M+Na+) | (M+H$^+$) 675.3 |

EXAMPLE 39

The Boc-protected amine (0.66 mmol) was dissolved in 6 mL 1:1 mixtures of DCM:TFA. The reaction was stirred for 60 min, and the solvent was removed under vacuum. The crude product was left under vacuum overnight before use (95%).

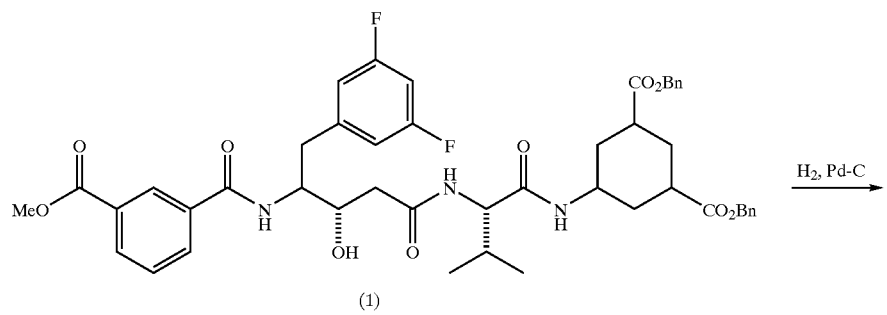

(1)

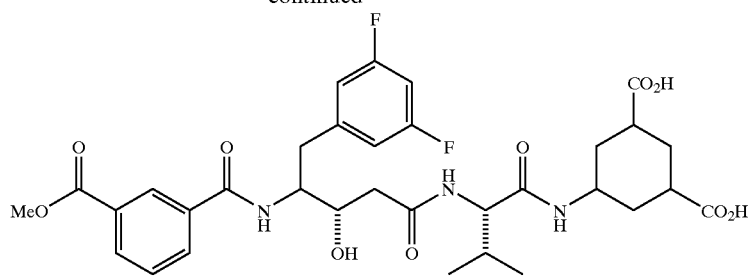

Procedure for Benzyl Ester

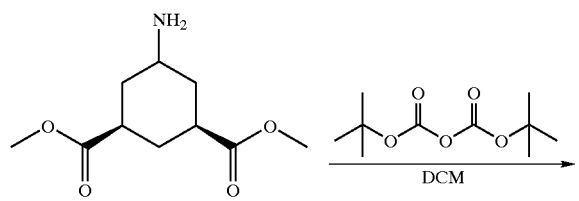

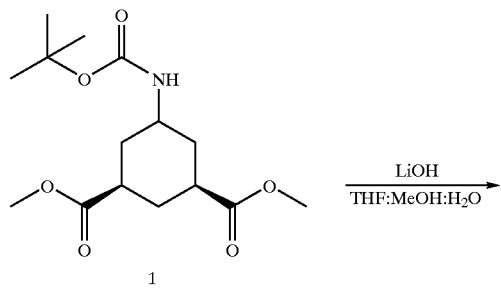

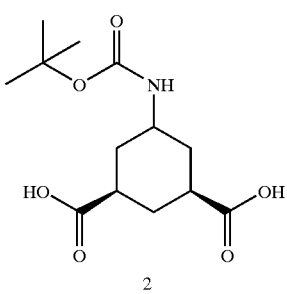

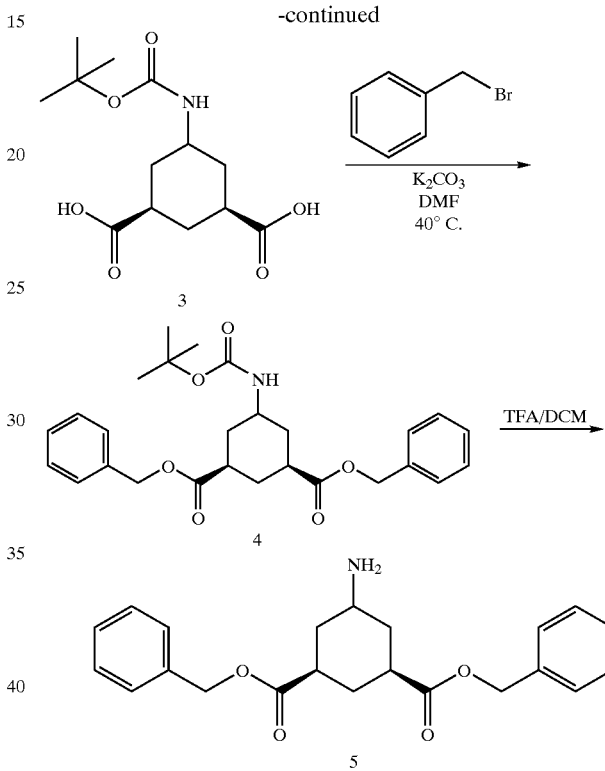

The di-benzyl ester (1) (1 equiv, 0.467 mmol) was transferred to a 14 mL reaction vial with septum and dissolved in a minimum amount of THF. The solution was de-gassed by bubbling $N_2$ via pipette before the addition of palladium on carbon (Pd—C). The mixture was again de-gassed before the cap with septum was replaced, and a disposable needle was placed through the septum to allow $H_2$ gas into the vial. The vial was placed into a parr shaker bottle, and the bottle was packed with a paper towel to avoid bumping of the vial on the sides of the bottle while shaking. After being placed into the parr shaker, the reaction was allowed to shake for 5 h at ambient temperature under an $H_2$ atmosphere of 50 psi. After 5 h, the reaction was filtered through celite and the solvents were removed in vacuo to give the crude white solid. (90% yield)

The amine (7.1 mmol) was dissolved in 20 mL of DCM before the addition of Boc-anhydride. The reaction was stirred overnight under nitrogen. The crude reaction was concentrated in a rotary evaporator to dryness. The white solid was chromatographed on is silica gel (60:40 Hexanes:EtOAc) to give compound 1, 1.38 g(66%).

The 5-(isopropoxymethyl-amino)-cyclohexane-1,3-dicarboxylic acid monomethyl ester (4.33 mmol) was then treated with $LiOH.H_2O$ (8.67 mmol) in a minimum amount of 1:2:1 THF:MeOH:$H_2O$ and allowed to stir overnight at ambient temperature. After 12 h, the solvents were removed under vacuum and subsequently partitioned between $H_2O$ and ethyl acetate. If emulsions prohibit separation of the two layers, a small amount of brine was added to aid in separation. The aqueous layer was extracted once more with ethyl acetate (to remove any unreacted starting material). The aqueous layer was then acidified with concentrated 10% aqueous citric acid. The cloudy-white acidic aqueous solution thus obtained was then extracted three times with ethyl acetate. These combined organic extracts were dried over anhydrous $MgSO_4$ or $NaSO_4$. Filtration of the drying agent and removal of solvents under vacuum gave the crude white solid. (90–100% yield).

The bis-acid (3.6 mmol) was dissolved in 4 mL of dry DMF, before the addition of carbonate. The mixture was stirred at 60° C., for 20 minutes, followed by the addition of the benzyl bromide. The reaction was stirred overnight at 45–60° C. The reaction then diluted with cold water then extracted using ether/water (3×). The combined organic layers were washed with 10% aqueous citric acid, saturated aqueous NaHCO$_3$, and brine. The extract is dried with anhydrous sodium sulfate, and evaporated to dryness. The oil residue was chromatographed on silica gel(80:20 hexanes:EtOAc) to give compound 4 (96%).

| | |
|---|---|
| Molecular Formula | $C_{33}H_{39}F_2N_3O_{10}$ |
| Molecular Weight | 675.67 |
| H-nmr (solvent) | (CD$_3$OD) δ 8.39(s, 1H, aryl), 8.14(d, 1H, aryl), 7.97(d, 1H, aryl), 7.55(t, 1H, aryl), 6.91–6.61(m, 3H, aryl), 4.42–4.35(m, 1H), 4.15–4.12(m, 2H), 3.93(s, 3H, OCH$_3$) 3.9–3.7(m, 1H), 3.1–2.9(m, 1H), 2.5–2.4(m, 4H), 2.3–1.7(m, 5H), 1.42–1.2 (m, 4H), 0.94–0.90(m, 6H, CH$_3$ × 2) |
| C-nmr (solvent) | |
| Mass spec (M+Na+) | (M+Na$^+$) 698.2 |

EXAMPLE 40

2-Methoxy mandelic acid was coupled using EDC coupling to the N-terminal of the functionalized dipeptide.

| | |
|---|---|
| Molecular Formula | $C_{32}H_{39}F_2N_3O_9$ |
| Molecular Weight | 647.27 |
| H-nmr (solvent) | (CD$_3$OD:CDCl$_3$ 1:1) δ 8.43(d, 1H, NH), 8.15(d, 1H, NH), 7.89(d, 1H, aryl), 7.47(m, 1H, aryl), 7.11–7.00(m, 2H, aryl), 6.91–6.86(m, 2H, aryl), 6.71–6.65(m, 1H, aryl), 4.37–4.32(m, 1H), 4.14–4.05(m, 2H), 3.97(s, 3H, OCH$_3$) 3.86–3.70 (m, 1H), 2.99–2.95(m, 2H), 2.49–2.41(m, 4H), 2.24–2.02(m, 4H), 1.47–1.27(m, 4H), 0.96–0.89 (m, 6H, CH$_3$ × 2) |
| Mass spec (M+Na+) | (M+H$^+$) 648.0 |

EXAMPLE 41

4-Methoxy mandelic acid (Lancaster Synthesis, Inc.) was coupled using EDC coupling to the N-terminal of the functionalized dipeptide.

| | |
|---|---|
| Molecular Formula | $C_{32}H_{39}F_2N_3O_9$ |
| Molecular Weight | 647.27 |
| H-nmr (solvent) | (CD$_3$OD) δ 7.85–7.7(m, 3H, aryl), 6.98–6.85(m, 3H, aryl), 6.75–6.62(m, 1H, aryl), 4.40–4.30(m, 1H), 4.20–4.10(m, 2H), 3.83(s, 3H, OCH$_3$) 3.83–3.7(m, 1H), 3.1–2.9(m, 2H), 2.5–2.4(m, 4H), 2.25–2.0(m, 4H), 1.5–1.2(m, 4H), 0.94–0.87 (m, 6H, CH$_3$ × 2) |
| Mass spec (M+Na+) | (M+Na$^+$) 670.4 |

EXAMPLE 42

Benzoic acid was coupled to the N-terminal of the dipeptide using standard EDC coupling.

| | |
|---|---|
| Molecular Formula | $C_{31}H_{37}F_2N_3O_8$ |
| Molecular Weight | 617.64 |
| H-nmr (solvent) | (CD$_3$OD) δ 7.79–7.40(m, 5H, aryl), 6.91–6.62(m, 3H, aryl), 4.4–4.3 m, 1H), 4.13–4.12(m, 2H), 3.82–3.75(m, 1H), 3.1–2.9(m, 2H), 2.5–2.4(m, 4H), 2.3–2.0(m, 4H), 1.5–1.2(m, 4H), 0.94–0.90(m, 6H, CH$_3$ × 2) |
| Mass spec (M+Na+) | (M+H$^+$) 618.3 |

EXAMPLE 43

2-naphthoic acid was coupled to the N-terminal of the dipeptide using standard EDC coupling.

| | |
|---|---|
| Molecular Formula | $C_{35}H_{39}F_2N_3O_8$ |
| Molecular Weight | 695.75 g/mol |
| Purification: | Column Chromatography |
| H-nmr (solvent) | (CDCl$_3$:CD$_3$OD 1:1) δ 8.9(d, 1H), 8.2(d, 1H), 8.1 (d, 1H), 7.93–7.39(m, 7H), 6.96–6.70(m, 3H), 4.6–4.4(m, 1H), 4.3–4.1(m, 2H), 4.0–3.9(m, 1H), 3.8–3.7(m, 1H), 3.1–2.9(m, 2H), 2.75–2.5(m, 2H), 2.5–2.3(m, 2H), 2.3–2.05(m, 2H), 1.4–1.2(m, 6H), 1.0–0.9(m, 6H) |
| Mass spec (M+Na+) | (M+Na$^+$) 689.8 |

EXAMPLE 44

4-methylcinnoline is oxidized to 4-carboxycinnoline and then coupled to the 3,5-difluoroPhe/Sta-Val-Ala-Glu-Phe [SEQ ID NO:1].

EXAMPLE 45

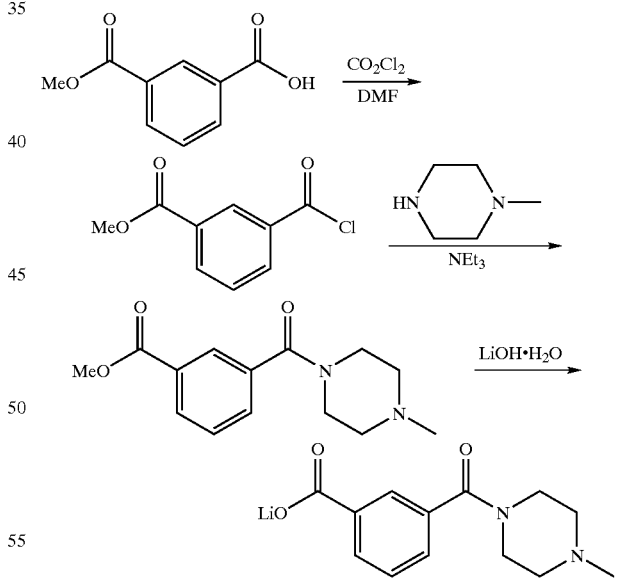

Methyl isophthalate (1.2 equiv, 2.78 mmol) was dissolved in dry CH2Cl2 and three drops of DMF (catalytic). The solution was cooled to 0° C. before the drop-wise addition of oxalyl chloride (2 equiv, 4.63 mmol). The mixture was stirred at 0° C. for 1 h. The mixture never dissolved. After 1 h, the solvents were removed in vacuo. The acid chloride was left under vacuum overnight.

The crude acid chloride (1 equiv, 2.78 mmol) was dissolved in dry CH$_2$Cl$_2$ and cooled to 0° C. before the addition of NEt$_3$ (5 equiv, 11.6 mmol) and N-methyl piperidine (6 equiv, 13.9 mmol). The reaction was stirred at 0° C. for 2 h before the solvents were removed in vacuo. The residue was diluted with H$_2$O and ethyl acetate and the layers were separated. The aqueous layer was extracted twice more with ethyl acetate, and the combined organic extracts were washed with saturated aqueous NaHCO$_3$, and dried over anhydrous MgSO$_4$. Filtration of the drying agent and removal of solvents in vacuo gave the clean crude product. (80% yield)

The crude amide (1 equiv, 2.19 mmol) was then treated with LiOH.H$_2$O (1 equiv, 2.19 mmol) in a minimum amount of 1:2:1 THF:MeOH:H$_2$O and allowed to stir overnight at ambient temperature. After 12 h, the solvents were removed in vacuo and subsequently partitioned between H$_2$O and ethyl acetate. The aqueous layer was extracted once more with ethyl acetate (to remove any unreacted starting material.) Removal of H$_2$O from aqueous layer in vacuo gave the crude white-yellow solid. (90–100% yield)

EXAMPLE 46

The N-terminal capping group was synthesized as described below.

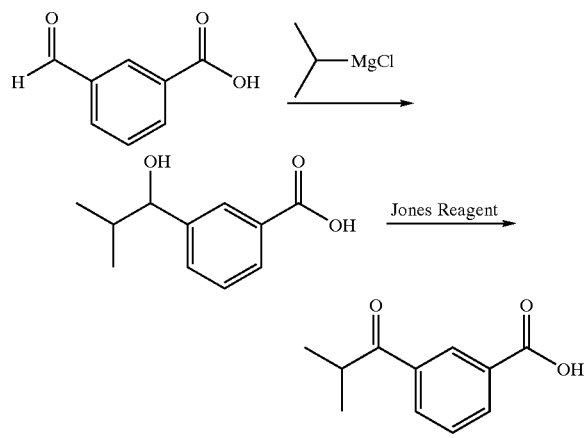

3-Carboxybenzaldehyde (1 equiv, 6.66 mmol, 1 g) was dissolved in THF (60 mL) and cooled to −78 C before the dropwise addition of a 2M solution isopropylmagnesium chloride (2 equiv, 13.32 mmol, 6.66 mL). Upon addition of the Grignard, a yellow-orange precipitate forms. The reaction was stirred for 1 h at −78 C. It this point, the progress of the reaction seemed slow, therefore more isopropylmagnesium chloride (0.2 equiv, 1.33 mmol, 0.67 mL) was added, and the reaction was stirred for an additional hour at 0 C before the reaction was quenched. The reaction was poured over ice-water and acidified with 6N HCl. This aqueous mixture was then treated with ethyl acetate, and the layers were separated. The aqueous layer was extracted twice more with ethyl acetate, and the combined organic extracts were washed with brine and dried over MgSO$_4$. Filtration of the drying agent and removal of the solvents in vacuo gave the crude yellow solid. Chromatography on silica gel with acetic acid:methanol:dichloromethane (1:3:96) gave the pure product. (30% yield)

The secondary alcohol (1 equiv, 1.04 mmol, 202.7 mg) was then dissolved in acetone before the dropwise addition of 2.5 M Jones Reagent (1 equiv, 1.04 mmol, 0.42 mL). (When the green color of the Jones Reagent persists, the reaction is finished.) The reaction was then gravity filtered and the filtrate was concentrated under reduced pressure to give the crude product. Chromatography on silica gel with acetic acid:methanol:dichloromethane (1:1:98) gave the pure product. (80% yield). This product was coupled with the 3,5-difluorophenylstatine-valine-3,5-dicarboxycyclohexylamide as in previous examples.

| | |
|---|---|
| Molecular Formula | C$_{35}$H$_{43}$F$_2$N$_3$O$_9$ |
| Molecular Weight | 687.74 |
| H-nmr (solvent) | (CD$_3$OD) δ 8.1(d, 1H, aryl), 7.95(d, 1H, aryl), 7.7 (d, 1H, aryl), 7.6(t, 1H, aryl), 6.9(d, 2H, aryl), 6.65(m, 1H, aryl), 4.4(m, 1H), 4.1(m, 2H), 3.8 (m, 1H), 3.6(m, 1H), 3.0(m, 2H), 2.4(m, 4H), 2.0 (m, 4H), 1.3(m, 4H), 1.2(m, 6H), 0.9 (m, 6H, CH$_3$ × 2) |
| Mass spec (M+Na+) | (M+Na$^+$) 710.4 |

EXAMPLE 47

1,6-Dimethylpyridine-3,5-dicarboxylic acid (Aldrich) was converted to the mono amide via the general procedure for C-terminal benzamides described in Example 22 and coupled with 3,5-difluorophenylstatine-valine-3,5-dicarboxycyclohexylamide as in previous examples.

| | |
|---|---|
| AN: | 92023 |
| Molecular Formula | C$_{41}$H$_{57}$F$_2$N$_5$O$_9$ |
| Molecular Weight | 773.86 |
| H-nmr (solvent) | (CD$_3$OD) δ 8.4(d, 1H, NH), 8.2(d, 1H, NH), 8.1 (d, 1H, NH), 7.4(broad, 1H, aryl), 6.9(d, 2H, aryl), 6.8(m, 1H, aryl), 4.4(m, 1H), 4.2(m, 2H), 3.8(m, 1H), 3.5(m, 2H), 3.0(m, 4H), 2.4(s, 6H, CH$_3$ × 2), 2.4(m, 4H), 2.1(m, 4H), 1.7(q, 2H), 1.5(q, 2H), 1.3(m, 3H), 1.0(m, 9H, CH$_3$ × 3), 0.7(t, 3H, CH$_3$) |
| Mass spec (M+H+) | (M+H$^+$) 774.9 |

EXAMPLE 48

2-Methoxyisophthalic acid (Aldrich) was converted to the mono amide via the general procedure for C-terminal benzamides described in Example 22 and coupled with 3,5-difluorophenylstatine-valine-3,5-dicarboxycyclohexylamide as in previous examples.

| | |
|---|---|
| Molecular Formula | C$_{37}$H$_{49}$F$_2$N$_4$O$_{10}$ |
| Molecular Weight | 746.79 |
| H-nmr (solvent) | (CD$_3$OD) δ 8 7.9(m, 1H, aryl), 7.35(m, 1H, aryl), 7.25(t, 1H, aryl), 6.9(m, 2H, aryl), 6.65(m, 1H, aryl), 4.4(m, 1H), 4.1(m, 2H), 3.8(s, 3H), 3.8(m, 1H), 3.4(m, 1H), 3.2(m, 2H), 3.0(m, 2H), 2.5(m, 4H), 2.1(m, 4H), 1.4(m, 4H), 1.3(t, 3H) 0.9(m, 6H, CH$_3$ × 2) |
| Mass spec (M+Na+) | (M+Na$^+$) 769.4 |

EXAMPLE 49

5-Methoxyisophthalic acid (Ubichem plc, Eastleigh, Hants SO53 4AR, UK/www.ubichem.com) was converted to the mono amide via the general procedure for C-terminal benzamides described in Example 22 and coupled with 3,5-difluorophenylstatine-valine-3,5-dicarboxycyclohexylamide as in previous examples.

| | |
|---|---|
| Molecular Formula | $C_{39}H_{52}F_2N_4O_{10}$ |
| Molecular Weight | 774.85 |
| H-nmr (solvent) | (CD$_3$OD) δ 7.4(s, 1H, aryl), 7.3(s, 1H, aryl), 7.0 (s, 1H, aryl), 6.9(d, 2H, aryl), 6.7(t, 1H, aryl), 4.4(m, 1H), 4.1(m, 2H), 3.9(s, 3H), 3.8(m, 1H), 3.5(m, 2H), 3.2(m, 2H), 3.0(m, 2H), 2.5(m, 4H), 2.2(m, 4H), 1.7(q, 2H), 1.6(q, 2H), 1.4(m, 3H), 1.0(m, 9H, CH$_3$ × 3), 0.7(t, 3H, CH$_3$) |
| Mass spec (M+Na+) | (M+Na$^+$) 798.4 |

The 5-hydroxyphenol may be prepared from the 5-methoxy isophthalic monoamide as follows:

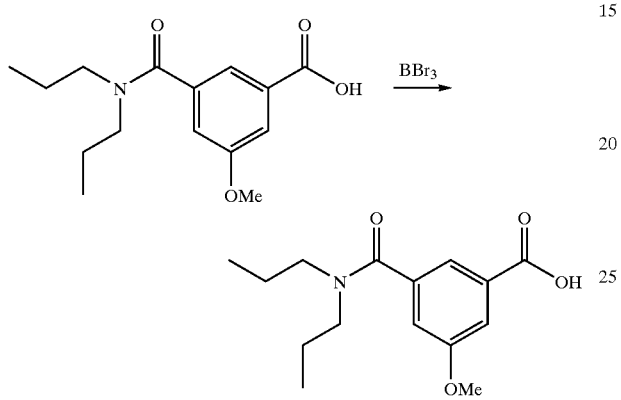

5-Methoxy isophthalic monoamide (1 equiv, 0.98 mmol, 0.273 g) was dissolved in CH$_2$Cl$_2$ (10 mL) and cooled to −78 C before the addition of 1M BBr$_3$ (3.5 equiv, 3.4 mL). The reaction was stirred for 45 minutes at −78 C, then 1.5 h at 0 C, then 1 h at ambient temperature. The reaction was then cooled to 0 C again, poured over ice-water, and acidified with 6N HCl. This aqueous mixture was then treated with ethyl acetate, and the layers were separated. The aqueous layer was extracted twice more with ethyl acetate, and the combined organic extracts were washed with brine and dried over MgSO$_4$. Filtration of the drying agent and removal of the solvents in vacuo gave the crude yellow solid. Purification via SiO$_2$ prep plate with acetic acid:methanol:dichloromethane (1:5:94) gave the pure white solid. (90% yield)

EXAMPLE 50

2,5-furandicarboxylate methyl ester (Aldrich) was converted to the mono amide via the general procedure for C-terminal benzamides described in Example 22 and coupled with 3,5-difluorophenylstatine-valine-3,5-dicarboxycyclohexylamide as in previous examples.

| | |
|---|---|
| Molecular Formula | $C_{36}H_{48}F_2N_4O_{10}$ |
| Molecular Weight | 734.78 |
| H-nmr (solvent) | (CD$_3$OD) δ 8.2(m, 1H, NH), 7.2(d, 1H, aryl), 7.0 (d, 1H, aryl), 6.9(m, 2H, aryl), 6.7(m, 1H, aryl), 4.4(m, 1H), 4.1(m, 2H), 3.8(m, 1H), 3.5(m, 4H), 3.0(m, 2H), 2.5(m, 4H), 2.2(m, 4H), 1.7(m, 4H), 1.4(m, 3H), 0.9(m, 12H) |
| Mass spec (M+H+) | (M+H$^+$) 734.78 |

EXAMPLE 51

2,5-thiophenedicarboxylic acid (Aldrich) was converted to the mono amide via the general procedure for C-terminal benzamides described in Example 22 and coupled with 3,5-difluorophenylstatine-valine-3,5-dicarboxycyclohexylamide as in previous examples.

| | |
|---|---|
| AN: | 92025 |
| Molecular Formula | $C_{36}H_{48}F_2N_4O_9S$ |
| Molecular Weight | 750.85 |
| H-nmr (solvent) | (CD$_3$OD) δ 8.2(d, 1H, NH), 8.1(d, 1H, NH), 7.7 (d, 0.5H, NH), 7.7 d 1H, aryl), 7.6(m, 0.5H, NH), 7.3(d, 1H, aryl), 6.9(d, 2H, aryl), 6.7(m, 1H, aryl), 4.4(m, 1H), 4.2(m, 2H), 3.8(m, 1H), 3.4 (t, 4H), 3.0(m, 2H), 2.5(m, 4H), 2.1(m, 4H), 1.7 (m, 4H), 1.4(m, 3H), 0.9(m, 12H) |
| Mass spec (M+H+) | (M+H$^+$) 751.9 |

EXAMPLE 52

3,4,5-trimethoxyaniline was hydrogenated via the procedure given for 3,5-dicarboxy-aniline to provide 2,3,4-trimethoxycyclohexylamine which was coupled to the C-terminal valine in the standard way.

| | |
|---|---|
| Molecular Formula | $C_{40}H_{58}F_2N_4O_8$ |
| Molecular Weight | 760 |
| Tlc (Rf(solvent) | Rf = 0.60 (10% MeOH/DCM) |
| Purification: | 1. Acid/Base washes |
| | 2. 2. Trituration/Filtration |
| Mass spec (MH+) | 761.3 (M+H, APCI-positive mode) |

EXAMPLE 53

The 3-trifluoromethylbenzylstatine derivative was synthesized using the procedure shown in Scheme III, starting with the specialty amino acid 3-trifluoromethylphenylalanine.

| | |
|---|---|
| Molecular Formula | C37 H42 F3 N3 O9 |
| Molecular Weight | 729 |
| tlc Rf (solvent) | 0.1(20% MeOH/CH2Cl2) |
| Purification: | Acid/base extraction |
| H-nmr (solvent) | (1:1 CD3OD:CDCl3) δ 8.35–8.10(m, 1H), 8.05–7.65(m, 3H), 7.65–7.20(m, 9.5H), 7.10–6.90(m, 0.5H), 5.78(s, 0.5H), 5.67(s, 0.5H), 4.40–4.00 (m, 3H), 3.90–3.60(m, 1H), 3.25–2.85(m, 2H), 2.60–1.80(m, 8H), 1.50–1.10(m, 3H), 0.95 (t, J=5.8Hz, 3H), 0.83(d, J=6.6Hz, 1.5H), 0.68 (d, J=6.6Hz, 1.5H). |
| C-nmr (solvent) | (1:1 CD3OD:CDCl3) δ 176.2, 176.12, 176.06, 176.04, 173.6, 173.4, 171.9, 171.7, 170.7, 170.6, 138.61, 138.59, 135.4, 134.8, 133.6, 133.4, 132.2, 132.1, 130.9, 130.7, 130.3, 130.2, 129.9, 129.8, 128.5, 128.43, 128.38, 128.10, 128.07, 125.7, 125.5, 125.3, 125.2, 125.1, 124.7, 124.6, 123.8, 123.2, 122.8, 121.9, 71.8, 71.2, 68.3, 68.2, 58.3, 58.2, 53.2, 40.7, 39.9, 37.0, 36.9, 33.5, 33.3, 30.3, 30.0, 29.9, 18.44, 18.37, 17.2, 16.8. |
| Mass spec (M+H+) | (CI) 729.8 |
| Synthetic Route Description | Wuts ref., A, B, C, G |

EXAMPLE 54

N,N-di-n-propyl-3-formylbenzamide

To 2 g (13.3 mmole) of 3-formyl benzoic acid was coupled with di-n-propylamine via Method I to give 2.5 g of the title compound as a white solid.

3-N,N-di-n-propyl-carboxamido-benzyl-di-fluoro-PheStatine-Val-1-amino-3,5-cis,cis-dimethyl cyclohexyldicarboxylate To 0.27 g (1.17 mmole) of N,N-di-n-propyl-3-formylbenzamide in 25 ml of N,N-dimethyl-formamide (DMF) and 1 ml of acetic acid was added 0.42 g (0.78 mmole) of H-difluorophenylstatine-Val-1-amino-3,5-cis,cis-dimethyl cyclohexyldicarboxylate and 0.49 g (7.8 mmole) of sodium cyanoborohydride in 25 ml of DMF, the reaction was stirred at room temperature for 16 hrs. The mixture was then diluted with ethyl acetate and successfully washed with water, brine, dried and stripped off the solvents, flash column purification afforded 0.22 g of the desired reduced amide as a pale white solid.
3-N,N-di-n-propyl-carboxamidobenzyl-difluorophenylstatine-Val-1-amino-3,5-cis,cis-cyclohexyldicarboxylic acid To 0.14 g (0.185 mmole) of the above compound was hydrolyzed via method G and gave 0.1 g of the title compound as a pale white solid.

| | |
|---|---|
| Molecular Formula | C38H52F2N4O8 |
| Molecular Weight | 730 |
| tlc Rf (solvent) | Rf = 0.15 (10% MeOH/DCM) |
| Purification: | Silica gel purification |
| Mass spec (MH+) | 731.4 |

EXAMPLE 55
Enzyme Inhibition Assay

The inhibitory concentration data was obtained by use of the MBP-C125 assay, which determines the relative inhibition of β-secretase cleavage of an MPB-C125 substrate by the compounds assayed. Human brain β-Secretase from concentrated HiQ pool prepared Jul. 16, 1997 in 0.20% Triton was used in the assay.

Inhibition data was obtained from an ELISA which uses an anti-MBP capture antibody (on precoated and blocked 96-well high binding plates) followed by incubation with diluted enzyme reaction supernatant, incubation with an anti-SW192 specific biotinylated reporter antibody and incubation with streptavidin/alkaline phosphatase. Detection was effected by a fluorescent substrate signal on cleavage by the phosphatase. ELISA only detected cleavage following Leu 596 at the substrate's Swedish APP 751 mutation site.

Compounds were diluted in a 1:1 dilution series to a six-point concentration curve (two wells per concentration) which took up one 96-plate row per compound tested. Relative compound inhibition potency was determined by calculating the concentration of compound that showed a fifty-percent reduction in detected signal compared to the enzyme reaction signal in the control wells with no added compound.

Procedure

Each of the test compounds was weighed out into a vial and DMSO was added to make up a 10 mM solution. To obtain a final compound concentration of 200 μM at the high point of a 6-point dilution curve, 100 μL of the 10 mM solution was added to well C1 of a 96-well V-bottom plate. Fifty μL of DMSO was added to odd wells of row C across the plate and 1:1 serial dilutions were made. 10 μL of each dilution was added to each of two wells on row C of a corresponding V-bottom plate to which 190 μL of 52 mM NaOAc/7.9% DMSO, pH 4.5 were pre-added. The NaOAc diluted compound plate was spun down to pellet precipitant and 20 μL/well was transferred to a corresponding flat-bottom plate to which 30 μL of ice-cold enzyme-substrate mixture (2.5 μL MBP-C125 substrate, 0.03 μL enzyme and 24.5 ice cold 0.09% TX100 per 30 μl) was added. The compound concentration in the final enzyme reaction was thus 50 times less than the starting concentration. The final reaction mixture of 200 μM compound for the highest curve point was in 5% DMSO, 20 mM NaAc, 0.06% TX100, at pH 4.5. The enzyme reaction was started by warming the plates to 37° C. After 90 minutes at 37° C., 200 μL/well cold specimen diluent was added to stop the reaction and 20 μL/well was transferred to a corresponding α-MBP coated ELISA plate, containing 80 μL/well specimen diluent. This reaction was incubated overnight at 4° C. and the ELISA was developed the next day using a 2 hr. incubation with α-192SW followed by Streptavidin-AP conjugate and flourescent substrate. The signal was read on a fluorescent plate reader.

Methods for Treating Alzheimer's Disease and Other Diseases Characterized by Deposition of Aβ Peptide This invention also relates to a method of treatment for patients suffering from disorders or diseases which can be attributed to Aβ plaque formation as previously described and, more specifically, a method of treatment involving the administration of the β-secretase inhibitors of formula 1 as the active constituents.

Accordingly, the compounds of formula 1 can be used among other things in the treatment Alzheimer's disease, and in diseases and indications resulting from the over-expression of Aβ-peptide such as found in certain genetic defect diseases such as plaque formation associated with Trisomy 21 (Down's Syndrome) and Hereditary Cerebral Hemorrhage with Amyloidosis of the Dutch-Type (HCHWA-D). As mentioned above, compounds of formula 1 are useful in medicine since they are active as inhibitors of β-secretase. Accordingly another aspect, this invention concerns:

a method of management (by which is meant treatment or prophylaxis) of disease or conditions mediated by β-secretase in mammals, in particular in humans, which method comprises administering to the mammal an effective, amount of a compound of formula 1 above, or a pharmaceutically acceptable salt or ester thereof; and a compound of formula (I) for use in human or veterinary medicine, particularly in the management (by which is meant treatment or prophylaxis) of diseases or conditions mediated by β-secretase; and the use of a compound of formula (I) in the preparation of a composition for the management (by which is meant treatment or prophylaxis) of diseases or conditions mediated by β-secretase.

The disease or conditions referred to above include Alzheimer's disease, plaque formation associated with Trisomy 21 (Down's Syndrome) and Hereditary Cerebral Hemorrhage with Amyloidosis of the Dutch-Type (HCHWA-D).

For the treatment of diseases characterized by the over-production and deposition of Aβ-peptide, the compunds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. The compounds may be administered in an amount from about 0.1 mg/kg/day to about 500 mg/kg/day. Preferred amounts for daily administration are from about 1 mg/kg to about 50 mg/kg. It will be understood however, that the amount of the compound actually administered will be determined by a physician in the light of the relevant circumstances, including the condition to be treated, the chosen route of administration, the actual compound administered, the age, weight and response of the individual patient, the severity of the patient's symptoms, and the like. Compositions are provided that contain therapeutically effective amounts of the compounds of formula 1. The compounds are preferably formulated into suitable pharmaceutical preparations such as tablets, capsules or elixirs, for oral administration or in sterile solutions or suspensions for parenteral administration. Typically the compounds described above are formulated into pharmaceutical compositions using techniques and procedures well known in the art.

About 1 to 500 mg of a compound or mixture of compounds for Formula 1 or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

To prepare compositions, one or more compounds of formula 1 are mixed with a suitable pharmaceutically acceptable carrier. Upon mixing or addition of the compound(s), the resulting mixture may be a solution, suspension, emulsion or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action or have other action. The compounds may be formulated as the sole pharmaceutically active ingredient in the composition or may be combined with other active ingredients.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween®, or dissolution in aqueous sodium bicarbonate. Derivatives of the compounds, such as salts of the compounds or prodrugs of the compounds may also be used in formulating effective pharmaceutical compositions.

The concentrations of the compounds are effective for delivery of an amount, upon administration, that ameliorates the symptoms of the disorder for which the compounds are administered. Typically, the compositions are formulated for single dosage administration.

The compounds of formula 1 may be prepared with carriers that protect them against rapid elimination from the body, such as time release formulations or coatings. Such carriers include controlled release formulations, such as, but not limited to, microencapsulated delivery systems, The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compositions can be enclosed in ampoules, disposable syringes or multiple or single dose vials made of glass, plastic or other suitable material. Such enclosed compositions can be provided in kits.

The concentration of active compound in the drug composition will depend on absorption, inactivation and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as, but not limited to, gum tragacanth, acacia, corn starch or gelatin; an excipient such as microcrystalline cellulose, starch and lactose, a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action.

Solutions or suspensions used for parenteral, intradermal, subcutaneous, or topical application can include any of the following components: a sterile diluent, such as water for injection, saline solution, fixed oil, a naturally occurring vegetable oil like sesame oil, coconut oil, peanut oil, cottonseed oil, etc. or a synthetic fatty vehicle like ethyl oleate or the like, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or multiple dose vials made of glass, plastic or other suitable material. Buffers, preservatives, antioxidants and the like can be incorporated as required.

If administered intravenously, suitable carriers include physiological saline or phosphate buffered saline (PBS), and solutions containing thickening and solubilizing agents, such as glucose, polyethylene glycol, and polypropyleneglycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art While this invention has been described with respect to various specific examples and embodiments, it is to be understood that the invention is not limited thereby and should only be construed by interpretation of the scope of the appended claims.

We claim:

1. A compound of formula 1

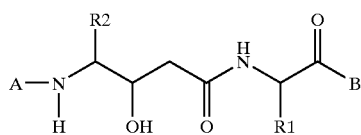

Formula 1 wherein:

A is

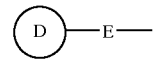

wherein D is chosen from aryl having 5 to 6 atoms; heteroaryl having 5 to 6 atoms where 1 or 2 heteroatoms are selected from N, O, and S; fused aryl of 8 to 14 atoms; fused heteroaryl of 8 to 14 atoms where 1, 2, or 3 heteroatoms are selected from N, O, and S; mono or fused cycloalkyl having 5 to 12 carbon atoms; and mono or fused heterocycloalkyl having 5 to 12 carbon atoms where 1, 2, or 3 heteroatoms are selected from N, O, and S; biaryl, diaryl ether; diarylketone, and phenyl ($C_1$–$C_8$) alkyloxyaryl;

and wherein E is a divalent group chosen from carbonyl, sulfonyl, $C_1$–$C_3$ alkylene, —X—($C_1$–$C_3$) alkylcarbonyl wherein X is chosen from N, O and S, or E is merely a bond;

and D may optionally be substituted with up to two groups chosen from OH, $C_1$–$C_3$ alkyl; $C_1$–$C_6$ alkylacylamino, $C_1$–$C_6$ alkylacyloxy, $C_1$–$C_6$ alkyloxy, $C_1$–$C_6$ alkylthioxy, amido, $NH_2$, mono and di($C_1$–$C_6$ alkyl and phenyl) amino, carbamyl, benzamides, carbamic acid esters, carboxyl, carboxy ($C_2$–$C_5$)alkyloxy, N-heterocyclylacyl, $C_1$–$C_3$ alkylsulfonyl, sulfonamide and $C_1$–$C_3$ alkylsulfonamide;

B is selected from —OH; $C_1$–$C_6$ alkyl or $C_1$–$C_6$ alkyl amino, di($C_1$–$C_6$ alkyl)amino, $C_1$–$C_6$ alkyloxy, N-heterocyclic and

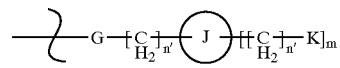

each n' is independently 0, 1 or 2;
m is 0, 1, 2 or 3;
and G is NH or O;
J is selected from the group consisting of aryl having a 5 to 6 membered ring; aryl having a 5 to 6 membered ring with 1, or 2 heteroatoms selected from N, O, and S; fused aryl rings of 8 to 14 atoms; fused aryl rings of 8 to 14 atoms with 1, 2, or 3 heteroatoms selected from N, O, and S; mono or fused ring cycloalkyl having 5 to 12 carbon atoms; and mono or fused ring heterocyclic having 5 to 12 carbon atoms with 1, 2, or 3 heteroatoms chosen from the group consisting of N, O, and S;
each K is chosen from OH, $C_1$–$C_3$ alkyl; $C_1$–$C_6$ alkylacylamino, $C_1$–$C_6$ alkylacyloxy, $C_1$–$C_6$ alkyloxy, $C_2$–$C_6$ alkylthioxy, amido, $NH_2$, mono and di($C_1$–$C_6$ alkyl and phenyl) amino, carbamyl; phenyl amides, carbamates, carboxyl and carboxy($C_2$–$C_5$) alkyloxy;
R1 is straight or branched chain $C_1$–$C_5$ alkanyl or $C_2$–$C_5$ alkenyl;
R2 is $C_{1-5}$ straight or branched chain alkanyl or alkenyl; methylthiomethyl; aryl or arylalkyl or heteroaryl or heteroarylalkyl wherein any of the above are optionally substituted with up to 2 of $C_{1-3}$ alkyl, trifluoromethyl or halogen, or a stereoisomer, hydrate or pharmaceutically acceptable salts thereof.

2. The compound of claim 1 wherein A is selected from biphenyl, 2-phenyl-α-hydroxytolyl, diphenyl ether and diphenyl ketone.

3. The compound of claim 1 wherein A is

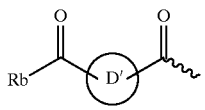

wherein the ring D' is a 5 or 6 membered monocyclic aryl or heteroaryl ring including up to 3 atoms selected from N, O and S, and Rb is —NH$_2$, mono and di(C$_2$–C$_6$ alkyl) amino, C$_1$–C$_6$ alkoxy, N-heterocyclic and C$_1$–C$_6$ alkyl.

4. The compound of claim 3 wherein R1 is 2-propyl and R2 is 3,5-difluorophenylmethyl.

5. The compound of claim 3 wherein the ring D' is chosen from the group consisting of benzene, pyridine, furan, thiophene, thiazole, thiadiazole, oxazole, oxadiazole and 1,2,4-triazole and Rb is di(C$_2$–C$_4$)alkylamine.

6. The compound of claim 1 wherein R1 is selected from ethyl and 2-propyl.

7. The compound of claim 1 wherein R2 is selected from 2-thienylmethyl, 3-trifluoromethylphenylmethyl, 4-thiazolylmethyl, 3-chlorophenylmethyl, 3,5-difluorophenylmethyl, 4-methylphenylmethyl and 2-methylprop-1-yl.

8. The compound of claim 1 wherein R1 is 2-propyl and R2 is 3,5-difluorophenylmethyl.

9. The compound of claim 1 wherein R1 is 2-propyl and R2 is 3,5-difluorophenylmethyl.

10. The compound of claim 1 wherein R1 is 2-propyl and R2 is 3,5-difluorophenylmethyl.

11. The compound of claim 1 wherein B is —OH, C$_1$–C$_6$ alkoxy, mono and di(C$_1$–C$_6$) alkylamino, aminoC$_1$–C$_4$ alkyl-p-benzoic acid and C$_1$–C$_6$ alkyl and phenyl esters thereof and N-heterocyclic.

12. The compound of claim 1 wherein B is

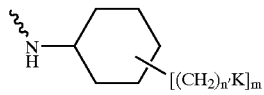

wherein K, n' and m are as defined in claim 1.

13. The compound of claim 12 wherein B is selected from 3,5-dicarboxycyclohexylamine, 3,4-dicarboxycyclohexylamine, 3,5-dimethoxycyclohexylamine, 3,5-dihydroxymethylcyclohexylamine and 3,4,5-trimethoxycyclohexylamine.

14. The compound of claim 1 wherein A is selected according to claim 3 and B is selected according to claim 11.

15. The compound of claim 1 wherein A is selected according to claim 5 and B is selected according to claim 12.

16. The compound of claim 1 wherein amido is selected from the group consisting of primary, C$_1$–C$_6$ alkyl, phenyl secondary and tertiary amido.

17. The compound of claim 1 wherein carbamyl is C$_1$–C$_6$ alkyl carbamyl.

18. The compound of claim 1 wherein carboxyl is selected from the group consisting of C$_1$–C$_6$ alkyl carboxyl and phenyl esters.

19. A compound selected from the group consisting of:

N-{N'-[2-hydroxy-2-(naphth-1-yl)ethanoyl]-(3S,4S)-4-amino-3-hydroxy-6-methylheptanoyl}valine (4-carboxy)phenylmethylamide N-{N'-[2-hydroxy-2-(naphth-1-yl)ethanoyl]-(3S,4S)-4-amino-3-hydroxy-6-methylheptanoyl}valine 2-[(4-carboxy)phenyl]ethylamide N-{N'-[2-hydroxy-2-(naphth-1-yl)ethanoyl]-(3S,4S)-4-amino-3-hydroxy-6-methylheptanoyl}valine 3-carboxypropylamide N-{N'-[2-hydroxy-2-(naphth-1-yl)ethanoyl]-(3S,4S)-4-amino-3-hydroxy-6-methylheptanoyl}valine 4-carboxynaphth-1-ylmethylamide N-{N'-[2-hydroxy-2-(naphth-1-yl)ethanoyl]-(3S,4S)-4-amino-3-hydroxy-6-methylheptanoyl}valine cis,cis-3,5-dicarboxycyclohexylamide N-{N'-[2-hydroxy-2-(naphth-1-yl)ethanoyl]-(3S,4S)-4-amino-3-hydroxy-6-methylheptanoyl}valine 4-carboxycyclohexylamide N-{N'-[2-hydroxy-2-(naphth-1-yl)ethanoyl]-(3S,4S)-4-amino-3-hydroxy-6-methylheptanoyl}valine N-{N'-[2-benzyloxy-2-(naphth-1-yl)ethanoyl]-(3S,4S)-4-amino-3-hydroxy-6-methylheptanoyl}valine (4-carboxy)phenylmethylamide N-[N'-(3-hydroxy-2-phenylpropanoyl)-(3S,4S)-4-amino-3-hydroxy-6-methylheptanoyl]valine (4-carboxy)phenylmethylamide N-{N'-[2-hydroxy-2-(2-bromophenyl)ethanoyl]-(3S,4S)-4-amino-3-hydroxy-6-methylheptanoyl}valine (4-carboxy)phenylmethylamide N-{N'-[(S)-2-hydroxy-3-phenylpropanoyl]-(3S,4S)-4-amino-3-hydroxy-6-methylheptanoyl}valine (4-carboxy)phenylmethylamide N-{N'-[2-hydroxy-2-(3-phenoxyphenyl)ethanoyl]-(3S,4S)-4-amino-3-hydroxy-6-methylheptanoyl}valine (4-carboxy)phenylmethylamide N-{N'-[(R)-2-hydroxy-3-phenylpropanoyl]-(3S,4S)-4-amino-3-hydroxy-6-methylheptanoyl}valine (4-carboxy)phenylmethylamide N-[N'-(3-hydroxy-3-phenylpropanoyl)-(3S,4S)-4-amino-3-hydroxy-6-methylheptanoyl]valine (4-carboxy)phenylmethylamide N-[N'-(3,3,3-trifluoro-2-methoxy-2-phenylpropanoyl)-(3S,4S)-4-amino-3-hydroxy-6-methylheptanoyl]valine (4-carboxy)phenylmethylamide N-{N'-[(R)-2-hydroxy-4-thiomethylbutanoyl]-(3S,4S)-4-amino-3-hydroxy-6-methylheptanoyl}valine (4-carboxy)phenylmethylamide N-[N'-(2-hydroxy-2-phenylethanoyl)-(3S,4S)-4-amino-3-hydroxy-6-methylheptanoyl]valine (4-carboxy)phenylmethylamide N-[N'-(2-hydroxy-2-phenylethanoyl)-(3S,4S)-4-amino-3-hydroxy-6-methylheptanoyl]valine (4-carboxy)phenylmethylamide N-{N'-[(2-hydroxy-2-(naphth-1-yl)ethanoyl]-(3S,4S)-4-amino-3-hydroxy-5-(4-methylphenyl)pentanoyl}valine (4-carboxy)phenylmethylamide N-{N'-[2-hydroxy-2-(naphth-1-yl)ethanoyl]-(3S,4S)-4-amino-3-hydroxy-5-(thien-2-yl)pentanoyl}valine (4-carboxy)phenylmethylamide N-{N'-[2-hydroxy-2-(naphth-1-yl)ethanoyl]-(3S,4S)-4-amino-3-hydroxy-5-(thiazol-4-yl)pentanoyl}valine (4-carboxy)phenylmethylamide N-{N'-[3-(N'',N''-diethylamido)benzoyl]-(3S,4S)-4-amino-3-hydroxy-5-(3,5-difluorophenyl)pentanoyl}valine cis,cis-3,5-dicarboxycyclohexylamide N-{N'-[3-(N''-ethyl-N''-methylamido)benzoyl]-(3S,4S)-4-amino-3-hydroxy-5-(3,5-difluorophenyl)pentanoyl}valine N-{N'-[3-(N''-ethyl-N''-methylamido)benzoyl]-(3S,4s)-4-amino-3-hydroxy-5-(3,5-difluorophenyl)pentanoyl}valine ethylamide N-{N'-[3-(N'',N''-diethylamido)benzoyl]-(3S,4S)-4-amino-3-hydroxy-5-(3,5-difluorophenyl)pentanoyl}valine N-{N'-[2-hydroxy-2-(naphth-1-yl)ethanoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(2-phenylphenyl)ethanoyl]-(3S,4S)-4-amino-3-hydroxy-5-(3,5-difluorophenyl)pentanoyl}valine ethylamide N-[N'-(4-N",N"-dimethylamino-5-oxopentanoyl)-(3S,4S)-4-amino-3-hydroxy-5-(3,5-difluorophenyl)pentanoyl]valine cis,cis-3,5-dicarboxycyclohexylamide N-{N'-[3-(N"-ethyl-N"-methylamido)benzoyl]-(3S,4S)-4-amino-3-hydroxy-5-(3,5-difluorophenyl)pentanoyl}valine cis,cis-3,5-dimethoxycyclohexylamide N-[N'-(benzo-1,4-dioxan-6-oyl)-(3S,4S)-4-amino-3-hydroxy-5-(3,5-difluorophenyl)pentanoyl]valine cis,cis-3,5-dicarboxycyclohexylamide N-[N'-(3-amidobenzoyl)-(3S,4S)-4-amino-3-hydroxy-5-(3,5-difluorophenyl)pentanoyl]valine cis,cis-3,5-dicarboxycyclohexylamide N-{N'-[3-(N"-acetylamino)benzoyl]-(3S,4S)-4-amino-3-hydroxy-5-(3,5-difluorophenyl)pentanoyl}valine cis,cis-3,5-dicarboxycyclohexylamide N-[N'-(3-carbomethoxybenzoyl)-(3S,4S)-4-amino-3-hydroxy-5-(3,5-difluorophenyl)pentanoyl]valine cis,cis-3,5-dicarboxycyclohexylamide N-{N'-[2-hydroxy-2-(2-methoxyphenyl)ethanoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(4-methoxyphenyl)ethanoyl]-(3S,4S)-4-amino-3-hydroxy-5-(3,5-difluorophenyl)pentanoyl}valine cis,cis-3,5-dicarboxycyclohexylamide N-[N'-benzoyl-(3S,4S)-4-amino-3-hydroxy-5-(3,5-difluorophenyl)pentanoyl]valine cis,cis-3,5-dicarboxycyclohexylamide N-[N'-(naphth-2-oyl)-(3S,4S)-4-amino-3-hydroxy-5-(3,5-difluorophenyl)pentanoyl]valine cis,cis-3,5-dicarboxycyclohexylamide N-{N'-[3-(N"-methylpiperazido)benzoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(4-methoxyphenyl)ethanoyl]-(3S,4S)-4-amino-3-hydroxy-5-(3-trifluoromethylphenyl)pentanoyl}valine cis,cis-3,5-dicarboxycyclohexylamide N-{N'-[3-(N",N"-dipropylamido)phenylmethyl]-(3S,4S)-4-amino-3-hydroxy-5-(3,5-difluorophenyl)pentanoyl}valine cis,cis,cis-3,4,5-trimethoxycyclohexylamide N-{N'-[5-(N",N"-dipropylamido)2,6-dimethylpyrid-3-ylcarbonyl]-(3S,4S)-4-amino-3-hydroxy-5-(3,5-difluorophenyl)pentanoyl}valine cis,cis-3,5-dicarboxycyclohexylamide N-{N'-[3-(N",N"-dipropylamido)-2-methyoxybenzoyl]-(3S,4S)-4-amino-3-hydroxy-5-(3,5-difluorophenyl)pentanoyl}valine cis,cis-3,5-dicarboxycyclohexylamide N-{N'-[3-(N",N"-dipropylamido)-5-methyoxybenzoyl]-(3S,4S)-4-amino-3-hydroxy-5-(3,5-difluorophenyl)pentanoyl}valine cis,cis-3,5-dicarboxycyclohexylamide N-{N'-[3-(2-methylpropionyl)-benzoyl]-(3S,4S)-4-amino-3-hydroxy-5-(3,5-difluorophenyl)pentanoyl}valine cis,cis-3,5-dicarboxycyclohexylamide N-{N'-[5-(N",N"-dipropylamido)-furan-2-ylcarbonyl]-(3S,4S)-4-amino-3-hydroxy-5-(3,5-difluorophenyl)pentanoyl}valine cis,cis-3,5-dicarboxycyclohexylamide N-{N'-[5-(N",N"-dipropylamido)-thiophen-2-ylcarbonyl]-(3S,4S)-4-amino-3-hydroxy-5-(3,5-difluorophenyl)pentanoyl}valine cis,cis-3,5-dicarboxycyclohexylamide N-{N'-[5-(N",N"-dipropylamido)-5-methylbenzoyl]-(3S,4S)-4-amino-3-hydroxy-5-(3,5-difluorophenyl)pentanoyl}valine cis,cis,cis-3,4,5-trimethoxycyclohexylamide N-{N'-[3-(N",N"-diethylamido)phenylmethyl]-(3S,4S)-4-amino-3-hydroxy-5-(3,5-difluorophenyl)pentanoyl}valine cis,cis-3,5-dicarboxycyclohexylamide N-[N'-(3-phenylbenzoyl)-(3S,4S)-4-amino-3-hydroxy-5-(3,5-difluorophenyl)pentanoyl]valine cis,cis-3,5-dicarboxycyclohexylamide, and N-[N'-2-pyrimidyl-(3S,4S)-4-amino-3-hydroxy-5-(3,5-difluorophenyl)pentanoyl]valine cis,cis-3,5-dicarboxycyclohexylamide.

20. A composition comprising a compound of formula 1

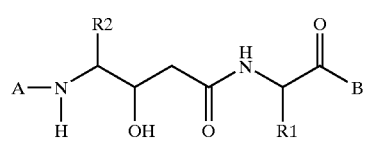

Formula 1 wherein:

A is

wherein D is chosen from aryl having 5 to 6 atoms; heteroaryl having 5 to 6 atoms where 1 or 2 heteroatoms are selected from N, O, and S; fused aryl of 8 to 14 atoms; fused heteroaryl of 8 to 14 atoms where 1, 2, or 3 heteroatoms are selected from N, O, and S; mono or fused cycloalkyl having 5 to 12 carbon atoms; and mono or fused heterocycloalkyl having 5 to 12 carbon atoms where 1, 2, or 3 heteroatoms are selected from N, O, and S; biaryl, diaryl ether; diarylketone, and phenyl($C_1$–$C_8$) alkyloxyaryl;

and wherein E is a divalent group chosen from carbonyl, sulfonyl, $C_1$–$C_3$ alkylene, —X—($C_1$–$C_3$) alkylcarbonyl wherein X is chosen from N, O and S, or E is merely a bond;

and D may optionally be substituted with up to two groups chosen from OH, $C_1$–$C_3$ alkyl; $C_1$–$C_6$ alkylacylamino, $C_1$–$C_6$ alkylacyloxy, $C_1$–$C_6$ alkyloxy, $C_1$–$C_6$ alkylthioxy, amido, $NH_2$, mono and di($C_1$–$C_6$ alkyl and phenyl) amino, carbamyl, benzamides, carbamic acid esters, carboxyl, carboxy ($C_2$–$C_5$)alkyloxy, N-heterocyclylacyl, $C_1$–$C_3$ alkylsulfonyl, sulfonamide and $C_1$–$C_3$ alkylsulfonamide;

B is selected from —OH; $C_1$–$C_6$ alkyl or $C_1$–$C_6$ alkyl amino, di($C_1$–$C_6$ alkyl)amino, $C_1$–$C_6$ alkyloxy, N-heterocyclic and

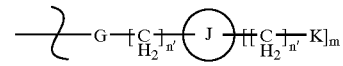

each n' is independently 0, 1 or 2;

m is 0, 1, 2 or 3;

and G is NH or O;

J is selected from the group consisting of aryl having a 5 to 6 membered ring; aryl having a 5 to 6 membered ring with 1, or 2 heteroatoms selected from N, O, and S; fused aryl rings of 8 to 14 atoms; fused aryl rings of 8 to 14 atoms with 1, 2, or 3 heteroatoms selected from N, O, and S; mono or fused ring cycloalkyl having 5 to 12 carbon atoms; and mono or fused ring heterocyclic having 5 to 12 carbon atoms with 1, 2, or 3 heteroatoms chosen from the group consisting of N, O, and S;

each K is chosen from OH, $C_1$–$C_3$ alkyl; $C_1$–$C_6$ alkylacylamino, $C_1$–$C_6$ alkylacyloxy, $C_1$–$C_6$ alkyloxy, $C_1$–$C_6$ alkylthioxy, amido, $NH_2$, mono and di($C_1$–$C_6$ alkyl and phenyl) amino, carbamyl; phenyl amides, carbamates, carboxyl and carboxy($C_2$–$C_5$) alkyloxy;

R1 is straight or branched chain $C_1$–$C_5$ alkanyl or $C_2$–$C_5$ alkenyl;

R2 is $C_{1-5}$ straight or branched chain alkanyl or alkenyl; methylthiomethyl; aryl or arylalkyl or heteroaryl or heteroarylalkyl wherein any of the above are optionally substituted with up to 2 of $C_{1-3}$ alkyl, trifluoromethyl or halogen, or a pharmaceutically acceptable salt or ester thereof and a pharmaceutically acceptable diluent.

21. The composition of claim 20 wherein A is selected from biphenyl, 2-phenyl-α-hydroxytolyl, diphenyl ether and diphenyl ketone.

22. The composition of claim 20 wherein A is

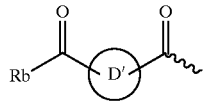

wherein the ring D' is a 5 or 6 membered monocyclic aryl or heteroaryl ring including up to 3 atoms selected from N, O and S, and Rb is —$NH_2$, mono and di($C_1$–$C_6$ alkyl) amino, $C_1$–$C_6$ alkoxy, N-heterocyclic and $C_1$–$C_6$ alkyl.

23. The composition of claim 22 wherein the ring D' is chosen from the group consisting of benzene, pyridine, furan, thiophene, thiazole, thiadiazole, oxazole, oxadiazole and 1,2,4-triazole and Rb is di($C_2$–$C_4$)alkylamine.

24. The composition of claim 22 wherein R1 is 2-propyl and R2 is 3,5-difluorophenylmethyl.

25. The composition of claim 20 wherein R1 is selected from ethyl and 2-propyl.

26. The composition of claim 20 wherein R2 is selected from 2-thienylmethyl, 3-trifluoromethylphenylmethyl, 4-thiazolylmethyl, 3-chlorophenylmethyl, 3,5-difluorophenylmethyl, 4-methylphenylmethyl and 2-methylprop-1-yl.

27. The composition of claim 20 wherein R1 is 2-propyl and R2 is 3,5-difluorophenylmethyl.

28. The composition of claim 20 wherein R1 is 2-propyl and R2 is 3,5-difluorophenylmethyl.

29. The composition of claim 20 wherein B is selected from the group consisting of —OH, $C_1$–$C_6$ alkoxy, mono and di($C_1$–$C_6$) alkylamino, amino$C_1$–$C_4$ alkyl-p-benzoic acid and $C_1$–$C_6$ alkyl and phenyl esters thereof, and N-heterocyclic.

30. The composition of claim 20 wherein B is

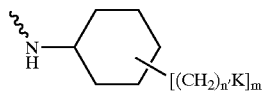

wherein K, n' and m are as defined in claim 1.

31. The composition of claim 20 wherein A is selected according to claim 22 and B is selected according to claim 30.

32. The composition of claim 30 wherein B is selected from 3,5-dicarboxycyclohexylamine, 3,4-dicarboxycyclohexylamine, 3,5-dimethoxycyclohexylamine, 3,5-dihydroxymethylcyclohexylamine and 3,4,5-trimethoxycyclohexylamine.

33. The composition of claim 20 wherein A is selected according to claim 22 and B is selected according to claim 29.

34. The composition of claim 20 wherein amido is selected from the group consisting of primary, $C_1$–$C_6$ alkyl, phenyl secondary and tertiary amido.

35. The composition of claim 20 wherein carbamyl is $C_1$–$C_6$ alkyl carbamyl.

36. The composition of claim 20 wherein carboxyl is selected from the group consisting of $C_1$–$C_6$ carboxyl and phenyl esters.

37. A composition comprising a compound selected from the group consisting of:

N-{N'-[2-hydroxy-2-(naphth-1-yl)ethanoyl]-(3S,4S)-4-amino-3-hydroxy-6-methylheptanoyl}valine (4-carboxy)phenylmethylamide N-{N'-[2-hydroxy-2-(naphth-1-yl)ethanoyl]-(3S,4S)-4-amino-3-hydroxy-6-methylheptanoyl}valine 2-[(4-carboxy)phenyl]ethylamide N-{N'-[2-hydroxy-2-(naphth-1-yl)ethanoyl]-(3S,4S)-4-amino-3-hydroxy-6-methylheptanoyl}valine 3-carboxypropylamide N-{N'-[2-hydroxy-2-(naphth-1-yl)ethanoyl]-(3S,4S)-4-amino-3-hydroxy-6-methylheptanoyl}valine 4-carboxynaphth-1-ylmethylamide N-{N'-[2-hydroxy-2-(naphth-1-yl)ethanoyl]-(3S,4S)-4-amino-3-hydroxy-6-methylheptanoyl}valine cis,cis-3,5-dicarboxycyclohexylamide N-{N'-[2-hydroxy-2-(naphth-1-yl)ethanoyl]-(3S,4S)-4-amino-3-hydroxy-6-methylheptanoyl}valine 4-carboxycyclohexylamide N-{N'-[2-hydroxy-2-(naphth-1-yl)ethanoyl]-(3S,4S)-4-amino-3-hydroxy-6-methylheptanoyl}valine N-{N'-[2-benzyloxy-2-(naphth-1-yl)ethanoyl]-(3S,4S)-4-amino-3-hydroxy-6-methylheptanoyl}valine (4-carboxy)phenylmethylamide N-[N'-(3-hydroxy-2-phenylpropanoyl)-(3S,4S)-4-amino-3-hydroxy-6-methylheptanoyl]valine (4-carboxy)phenylmethylamide N-{N'-[2-hydroxy-2-(2-bromophenyl)ethanoyl]-(3S,4S)-4-amino-3-hydroxy-6-methylheptanoyl}valine (4-carboxy)phenylmethylamide N-{N'-[(S)-2-hydroxy-3-phenylpropanoyl]-(3S,4S)-4-amino-3-hydroxy-6-methylheptanoyl}valine (4-carboxy)phenylmethylamide N-{N'-[2-hydroxy-2-(3-phenoxyphenyl)ethanoyl]-(3S,4S)-4-amino-3-hydroxy-6-methylheptanoyl}valine (4-carboxy)phenylmethylamide N-{N'-[(R)-2-hydroxy-3-phenylpropanoyl]-(3S,4S)-4-amino-3-hydroxy-6-methylheptanoyl}valine (4-carboxy)phenylmethylamide N-[N'-(3-hydroxy-3-phenylpropanoyl)-(3S,4S)-4-amino-3-hydroxy-6-methylheptanoyl]valine (4-carboxy)phenylmethylamide N-[N'-(3,3,3-trifluoro-2-methoxy-2-phenylpropanoyl)-(3S,4S)-4-amino-3-hydroxy-6-methylheptanoyl]valine (4-carboxy)phenylmethylamide N-{N'-[(R)-2-hydroxy-4-thiomethylbutanoyl]-(3S,4S)-4-amino-3-hydroxy-6-methylheptanoyl}valine (4-carboxy)phenylmethylamide N-[N'-(2-hydroxy-2-phenylethanoyl)-(3S,4S)-4-amino-3-hydroxy-6-methylheptanoyl]valine (4-carboxy)phenylmethylamide N-[N'-(2-hydroxy-2-phenylethanoyl)-(3S,4S) -4-amino-3-hydroxy-6-methylheptanoyl]valine (4-carboxy)phenylmethylamide N-{N'-[(2-hydroxy-2-(naphth-1-yl)ethanoyl]-(3S,4S)-4-amino-3-hydroxy-5-(4-methylphenyl)pentanoyl}valine (4-carboxy)phenylmethylamide N-{N'-[2-hydroxy-2-(naphth-1-yl)ethanoyl]-(3S,4S)-4-amino-3-hydroxy-5-(thien-2-yl)pentanoyl}valine (4-carboxy)phenylmethylamide N-{N'-[2-hydroxy-2-(naphth-1-yl)ethanoyl]-(3S,4S)-4-amino-3-hydroxy-5-(thiazol-4-yl)pentanoyl}valine (4-carboxy)phenylmethylamide N-{N'-[3-(N'',N''-diethylamido)benzoyl]-(3S,4S)-4-amino-3-hydroxy-5-(3,5-difluorophenyl)pentanoyl}valine cis,cis-3,5-dicarboxycyclohexylamide N-{N'-[3-(N''-ethyl-N''-methylamido)benzoyl]-(3S,4S)-4-amino-3-hydroxy-5-(3,5-difluorophenyl)pentanoyl}valine N-{N'-[3-(N''-ethyl-N''-methylamido)benzoyl]-(3S,4S)-4-amino-3-hydroxy-5-(3,5-difluorophenyl)pentanoyl}valine ethylamide N-{N'-[3-(N'',N''-diethylamido)benzoyl]-(3S,4S)-4-amino-3-hydroxy-5-(3,5-difluorophenyl)pentanoyl}valine N-{N'-[2-hydroxy-2-(naphth-1-yl)ethanoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(2-phenylphenyl)ethanoyl]-(3S,4S)-4-amino-3-hydroxy-5-(3,5-difluorophenyl)pentanoyl}valine ethylamide N-[N'-(4-N'',N''-dimethylamino-5-oxopentanoyl)-(3S,4S)-4-amino-3-hydroxy-5-(3,5-difluorophenyl)pentanoyl]valine cis,cis-3,5-dicarboxycyclohexylamide N-{N'-[3-(N''-ethyl-N''-methylamido)benzoyl]-(3S,4S)-4-amino-3-hydroxy-5-(3,5-difluorophenyl)pentanoyl}valine cis,cis-3,5-dimethoxycyclohexylamide N-[N'-(benzo-1,4-dioxan-6-oyl)-(3S,4S)-4-amino-3-hydroxy-5-(3,5-difluorophenyl)pentanoyl]valine cis,cis-3,5-dicarboxycyclohexylamide N-[N'-(3-amidobenzoyl)-(3S,4S)-4-amino-3-hydroxy-5-(3,5-difluorophenyl)pentanoyl]valine cis,cis-3,5-dicarboxycyclohexylamide N-{N'-[3-(N''-acetylamino)benzoyl]-(3S,4S)-4-amino-3-hydroxy-5-(3,5-difluorophenyl)pentanoyl}valine cis,cis-3,5-dicarboxycyclohexylamide N-[N'-(3-carbomethoxybenzoyl)-(3S,4S)-4-amino-3-hydroxy-5-(3,5-difluorophenyl)pentanoyl]valine cis,cis-3,5-dicarboxycyclohexylamide N-{N'-[2-hydroxy-2-(2-methoxyphenyl)ethanoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(4-methoxyphenyl)ethanoyl]-(3S,4S)-4-amino-3-hydroxy-5-(3,5-difluorophenyl)pentanoyl}valine cis,cis-3,5-dicarboxycyclohexylamide N-[N'-benzoyl-(3S,4S)-4-amino-3-hydroxy-5-(3,5-difluorophenyl)pentanoyl]valine cis,cis-3,5-dicarboxycyclohexylamide N-[N'-(naphth-2-oyl)-(3S,4S)-4-amino-3-hydroxy-5-(3,5-difluorophenyl)pentanoyl]valine cis,cis-3,5-dicarboxycyclohexylamide N-{N'-[3-(N''-methylpiperazido)benzoyl]-(3S,4S)-4-amino-3-hydroxy-5-(3,5-difluorophenyl)pentanoyl}valine cis,cis-3,5-dicarboxycyclohexylamide N-{N'-[2-hydroxy-2-(4-methoxyphenyl)ethanoyl]-(3S,4S)-4-amino-3-hydroxy-5-(3-trifluoromethylphenyl)pentanoyl}valine cis,cis-3,5-dicarboxycyclohexylamide N-{N'-[3-(N'',N''-dipropylamido)phenylmethyl]-(3S,4S)-4-amino-3-hydroxy-5-(3,5-difluorophenyl)pentanoyl}valine cis,cis,cis-3,4,5-trimethoxycyclohexylamide N-{N'-[5-(N'',N''-dipropylamido)2,6-dimethylpyrid-3-ylcarbonyl]-(3S,4S)-4-amino-3-hydroxy-5-(3,5-difluorophenyl)pentanoyl}valine cis,cis-3,5-dicarboxycyclohexylamide N-{N'-[3-(N'',N''-dipropylamido)-2-methyoxybenzoyl]-(3S,4S)-4-amino-3-hydroxy-5-(3,5-difluorophenyl)pentanoyl}valine cis,cis-3,5-dicarboxycyclohexylamide N-{N'-[3-(N'',N''-dipropylamido)-5-methyoxybenzoyl]-(3S,4S)-4-amino-3-hydroxy-5-(3,5-difluorophenyl)pentanoyl}valine cis,cis-3,5-dicarboxycyclohexylamide N-{N'-[3-(2-methylpropionyl)-benzoyl]-(3S,4S)-4-amino-3-hydroxy-5-(3,5-difluorophenyl)pentanoyl}valine cis,cis-3,5-dicarboxycyclohexylamide N-{N'-[5-(N'',N''-dipropylamido)-furan-2-ylcarbonyl]-(3S,4S)-4-amino-3-hydroxy-5-(3,5-difluorophenyl)pentanoyl}valine cis,cis-3,5-dicarboxycyclohexylamide N-{N'-[5-(N'',N''-dipropylamido)-thiophen-2-ylcarbonyl]-(3S,4S)-4-amino-3-hydroxy-5-(3,5-difluorophenyl)pentanoyl}valine cis,cis-3,5-dicarboxycyclohexylamide N-{N'-[5-(N'',N''-dipropylamido)-5-methylbenzoyl]-(3S,4S)-4-amino-3-hydroxy-5-(3,5-difluorophenyl)pentanoyl}valine cis,cis,cis-3,4,5-trimethoxycyclohexylamide N-{N'-[3-(N'',N''-diethylamido)phenylmethyl]-(3S,4S)-4-amino-3-hydroxy-5-(3,5-difluorophenyl)pentanoyl}valine cis,cis-3,5-dicarboxycyclohexylamide N-[N'-(3-phenylbenzoyl)-(3S,4S)-4-amino-3-hydroxy-5-(3,5-difluorophenyl)pentanoyl]valine cis,cis-3,5-dicarboxycyclohexylamide, and N-[N'-2-pyrimidyl-(3S,4S)-4-amino-3-hydroxy-5-(3,5-difluorophenyl)pentanoyl]valine cis,cis-3,5-dicarboxycyclohexylamide, and pharmaceutically acceptable salts and esters thereof, and a pharmaceutically acceptable diluent.

* * * * *